(12) United States Patent
Stowell et al.

(10) Patent No.: US 10,955,378 B2
(45) Date of Patent: *Mar. 23, 2021

(54) RESONANT GAS SENSOR

(71) Applicant: Lyten, Inc., Sunnyvale, CA (US)

(72) Inventors: Michael W. Stowell, Sunnyvale, CA (US); Bruce Lanning, Littleton, CO (US); Sung H. Lim, Mountain View, CA (US); Shreeyukta Singh, Sunnyvale, CA (US); John Chmiola, San Francisco, CA (US)

(73) Assignee: LytEn, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/706,542

(22) Filed: Dec. 6, 2019

(65) Prior Publication Data

US 2020/0256827 A1  Aug. 13, 2020

Related U.S. Application Data

(63) Continuation of application No. 16/239,423, filed on Jan. 3, 2019, now Pat. No. 10,502,705.

(Continued)

(51) Int. Cl.
*G01N 27/414*  (2006.01)
*C01B 32/182*  (2017.01)
(Continued)

(52) U.S. Cl.
CPC .... *G01N 27/4141* (2013.01); *B01J 20/28066* (2013.01); *C01B 32/182* (2017.08); *C01B 2204/04* (2013.01); *C01B 2204/22* (2013.01); *C01B 2204/32* (2013.01); *G01N 27/127* (2013.01); *G01N 27/4045* (2013.01); *G01N 29/036* (2013.01); *G01N 33/004* (2013.01);
(Continued)

(58) Field of Classification Search
CPC ......... G01N 27/4141; G01N 2291/014; G01N 27/127; G01N 33/004; G01N 27/4045; G01N 29/036; G01N 33/0037; G01N 33/0039; G01N 33/0044; B01J 20/28066; C01B 32/182

See application file for complete search history.

(56) References Cited

U.S. PATENT DOCUMENTS 3,706,445 A * 12/1972 Gentry ................. F26B 23/022
                                                          432/72
4,141,800 A *  2/1979 Breuer ............... G01N 27/4045
                                                          205/779.5

(Continued)

FOREIGN PATENT DOCUMENTS

WO  WO-2015083073 A1 *  6/2015  ......... H03H 9/02259
WO  WO-2019067488 A1 *  4/2019  .......... G01N 29/036

*Primary Examiner* — David A. Rogers
(74) *Attorney, Agent, or Firm* — Paradice & Li LLP

(57) ABSTRACT

A method for detecting an analyte comprises providing a first carbon-based material comprising reactive chemistry additives, providing conductive electrodes connected to the first carbon-based material, exposing the first carbon-based material to an analyte, applying a plurality of alternating currents having a range of frequencies across the conductive electrodes, and measuring the complex impedance of the first carbon-based material using the plurality of alternating currents.

20 Claims, 15 Drawing Sheets

Related U.S. Application Data

(60) Provisional application No. 62/613,716, filed on Jan. 4, 2018, provisional application No. 62/815,927, filed on Mar. 8, 2019.

(51) Int. Cl.
  *B01J 20/28* (2006.01)
  *G01N 33/00* (2006.01)
  *G01N 27/404* (2006.01)
  *G01N 29/036* (2006.01)
  *G01N 27/12* (2006.01)

(52) U.S. Cl.
  CPC ..... *G01N 33/0037* (2013.01); *G01N 33/0039* (2013.01); *G01N 33/0044* (2013.01); *G01N 2291/014* (2013.01)

(56) References Cited

U.S. PATENT DOCUMENTS

| | | | | |
|---|---|---|---|---|
| 4,701,317 A * | 10/1987 | Arakawa | C01B 32/20 | 423/445 R |
| 5,143,709 A * | 9/1992 | Labes | C04B 35/52 | 423/449.4 |
| 5,211,923 A * | 5/1993 | Harkness | C01B 3/04 | 423/220 |
| 5,324,553 A * | 6/1994 | Ovshinsky | C23C 16/511 | 427/250 |
| 5,515,011 A * | 5/1996 | Pasco | H03B 9/10 | 327/113 |
| 5,520,789 A * | 5/1996 | Takahashi | G01N 27/4075 | 204/424 |
| 5,556,475 A * | 9/1996 | Besen | C23C 16/511 | 118/723 E |
| 5,572,866 A * | 11/1996 | Loving | F01N 3/26 | 60/274 |
| 5,725,754 A * | 3/1998 | Belford | G01N 27/122 | 205/775 |
| 5,874,705 A * | 2/1999 | Duan | H01J 37/32009 | 156/345.41 |
| 6,019,284 A * | 2/2000 | Freeman | G02F 1/13452 | 235/375 |
| 6,156,114 A * | 12/2000 | Bell | B01J 8/0015 | 106/400 |
| 6,224,736 B1 * | 5/2001 | Miyamoto | C25D 9/08 | 205/97 |
| 6,340,912 B1 * | 1/2002 | Gerstenberg | H05B 6/666 | 327/126 |
| 6,383,301 B1 * | 5/2002 | Bell | B01J 8/0015 | 118/716 |
| 6,582,778 B2 * | 6/2003 | Namiki | C23C 16/045 | 427/237 |
| 6,805,779 B2 * | 10/2004 | Chistyakov | H01J 37/32321 | 204/298.36 |
| 6,914,556 B1 * | 7/2005 | Nyswander | G01S 7/282 | 331/87 |
| 6,916,400 B2 * | 7/2005 | Moisan | B01D 53/32 | 118/723 MA |
| 7,022,149 B2 * | 4/2006 | Krause | B01J 19/2485 | 48/61 |
| 7,102,110 B2 * | 9/2006 | Shinohara | H01J 23/34 | 219/702 |
| 7,400,253 B2 * | 7/2008 | Cohen | G06K 19/0707 | 235/383 |
| 7,608,798 B2 * | 10/2009 | Kumar | B01J 19/126 | 219/121.59 |
| 7,739,029 B2 * | 6/2010 | Ishikawa | G08G 1/096827 | 701/117 |
| 7,799,119 B2 * | 9/2010 | Zakrzewski | H05H 1/46 | 96/15 |
| 7,821,794 B2 * | 10/2010 | Pennaz | G09F 3/208 | 361/761 |
| 7,875,322 B2 * | 1/2011 | Kobayashi | H01L 21/31662 | 427/575 |
| 8,034,321 B2 * | 10/2011 | Mauthner | C01B 32/18 | 423/652 |
| 8,052,932 B2 * | 11/2011 | Han | B82Y 15/00 | 422/90 |
| 8,075,869 B2 * | 12/2011 | Zhu | C01B 3/26 | 423/650 |
| 8,114,375 B2 * | 2/2012 | Jang | C25B 1/00 | 423/448 |
| 8,222,579 B2 * | 7/2012 | Taguchi | H05B 6/806 | 219/745 |
| 8,337,764 B2 * | 12/2012 | Yang | C07C 2/76 | 422/186 |
| 8,475,760 B2 * | 7/2013 | Rajala | B82Y 40/00 | 423/447.1 |
| 8,508,193 B2 * | 8/2013 | Keating | H02J 50/001 | 320/137 |
| 8,603,402 B2 * | 12/2013 | Chang | H01J 37/32678 | 422/186.04 |
| 8,636,960 B2 * | 1/2014 | Spitzl | C01C 1/0417 | 422/186 |
| 8,754,454 B2 * | 6/2014 | Bryant | B82Y 30/00 | 257/253 |
| 8,808,507 B2 * | 8/2014 | Kasin | C10B 19/00 | 201/19 |
| 8,821,745 B2 * | 9/2014 | Luo | G01N 27/4145 | 216/83 |
| 8,933,629 B2 * | 1/2015 | Heil | H01J 37/32146 | 315/111.21 |
| 8,968,588 B2 * | 3/2015 | Zhao | H05H 1/46 | 216/69 |
| 9,038,443 B1 * | 5/2015 | Pace | G01H 13/00 | 73/64.53 |
| 9,051,185 B2 * | 6/2015 | Levendis | B82Y 40/00 | |
| 9,063,079 B2 * | 6/2015 | Eckhardt | G01N 27/413 | |
| 9,156,699 B2 * | 10/2015 | Yamada | C01B 32/186 | |
| 9,293,302 B2 * | 3/2016 | Risby | H05H 1/30 | |
| 9,395,343 B2 * | 7/2016 | Schmid | G01N 5/02 | |
| 9,471,862 B2 * | 10/2016 | Atkinson | G06K 19/07707 | |
| 9,612,690 B2 * | 4/2017 | Zirkl | G06F 3/0418 | |
| 9,678,036 B2 * | 6/2017 | Balandin | G01N 27/414 | |
| 9,705,469 B2 * | 7/2017 | Rinaldi | H03H 3/02 | |
| 9,735,279 B2 * | 8/2017 | Sato | G01N 27/127 | |
| 9,767,992 B1 * | 9/2017 | Stowell | H01J 37/32192 | |
| 9,862,602 B1 * | 1/2018 | Riso | C01B 32/20 | |
| 9,862,606 B1 * | 1/2018 | Cook | C01B 32/152 | |
| 9,869,651 B2 * | 1/2018 | Akinwande | G01N 27/125 | |
| 9,927,390 B2 * | 3/2018 | Satou | G01N 27/4077 | |
| 10,024,831 B2 * | 7/2018 | Ruhl | G01N 33/004 | |
| 10,031,097 B1 * | 7/2018 | Han | G01N 27/048 | |
| 2001/0020383 A1 * | 9/2001 | Moos | G01N 27/123 | 73/31.06 |
| 2003/0024806 A1 * | 2/2003 | Foret | C01B 3/22 | 204/164 |
| 2003/0138365 A1 * | 7/2003 | Obidniak | F23G 5/40 | 422/224 |
| 2004/0029339 A1 * | 2/2004 | Yamamoto | H01J 37/32192 | 438/222 |
| 2004/0261617 A1 * | 12/2004 | Stewart | C01B 3/38 | 95/96 |
| 2004/0265211 A1 * | 12/2004 | Dillon | B82Y 40/00 | 423/447.3 |
| 2005/0003247 A1 * | 1/2005 | Pham | H01M 8/0618 | 48/197 R |
| 2005/0163696 A1 * | 7/2005 | Uhm | H05B 6/806 | 423/445 B |
| 2005/0253529 A1 * | 11/2005 | Kumar | B01J 19/126 | 315/111.71 |
| 2007/0017136 A1 * | 1/2007 | Mosher, Jr. | G06K 19/07749 | 40/633 |
| 2007/0048181 A1 * | 3/2007 | Chang | G01N 27/4146 | 422/400 |
| 2007/0056352 A1 * | 3/2007 | Birkhofer | G01N 33/0006 | 73/23.21 |

(56) References Cited

U.S. PATENT DOCUMENTS

| | | | | |
|---|---|---|---|---|
| 2007/0212254 A1* | 9/2007 | Nagatsu | H01J 37/32568 | 422/21 |
| 2007/0274893 A1* | 11/2007 | Wright | H05H 1/30 | 423/449.1 |
| 2008/0029030 A1* | 2/2008 | Goto | H05H 1/46 | 118/723 R |
| 2009/0196801 A1* | 8/2009 | Mills | C23C 16/277 | 422/186 |
| 2009/0220767 A1* | 9/2009 | Schlogl | B01J 23/745 | 428/323 |
| 2009/0327188 A1* | 12/2009 | Ryhanen | G06K 9/00986 | 706/46 |
| 2010/0056819 A1* | 3/2010 | Jang | B82Y 30/00 | 556/478 |
| 2011/0033639 A1* | 2/2011 | Coll | C23C 16/50 | 427/585 |
| 2011/0036014 A1* | 2/2011 | Tsangaris | C10J 3/482 | 48/62 R |
| 2012/0006102 A1* | 1/2012 | Bryant | G01N 27/4146 | 73/61.43 |
| 2012/0034137 A1* | 2/2012 | Risby | H01J 37/32357 | 422/186.29 |
| 2012/0049864 A1* | 3/2012 | Han | G01N 27/127 | 324/649 |
| 2012/0058397 A1* | 3/2012 | Zhamu | H01M 4/13 | 429/231.8 |
| 2012/0094175 A1* | 4/2012 | Sheem | H01M 4/0471 | 429/207 |
| 2012/0258374 A1* | 10/2012 | Raston | B82Y 30/00 | 429/411 |
| 2013/0040397 A1* | 2/2013 | Star | B82Y 15/00 | 436/121 |
| 2013/0157729 A1* | 6/2013 | Tabe | H04W 52/0245 | 455/573 |
| 2013/0248773 A1* | 9/2013 | Chang | H01M 4/625 | 252/506 |
| 2013/0270110 A1* | 10/2013 | Sasai | H01J 37/32678 | 204/298.16 |
| 2014/0159572 A1* | 6/2014 | Risby | H05H 1/30 | 315/39.51 |
| 2014/0208638 A1* | 7/2014 | Van Thorre | C10G 1/02 | 44/307 |
| 2014/0251955 A1* | 9/2014 | Itoh | H01J 37/32211 | 216/69 |
| 2014/0260547 A1* | 9/2014 | Balandin | B82Y 15/00 | 73/31.06 |
| 2014/0263202 A1* | 9/2014 | Partridge | B23K 10/02 | 219/121.48 |
| 2014/0305191 A1* | 10/2014 | Schmid | G01N 9/002 | 73/24.03 |
| 2014/0336952 A1* | 11/2014 | Kellaway | G01N 27/123 | 702/24 |
| 2014/0353207 A1* | 12/2014 | Strohm | B01J 19/088 | 208/14 |
| 2015/0008486 A1* | 1/2015 | Bryant | G01N 33/497 | 257/253 |
| 2015/0044565 A1* | 2/2015 | Wang | H01M 4/1395 | 429/221 |
| 2015/0246813 A1* | 9/2015 | Koveal, Jr. | B82Y 40/00 | 423/445 R |
| 2015/0267063 A1* | 9/2015 | Drewer | A01C 1/06 | 47/57.6 |
| 2015/0323482 A1* | 11/2015 | Shimoyama | G01N 27/125 | 73/31.06 |
| 2015/0377824 A1* | 12/2015 | Ruhl | G01N 27/127 | 204/424 |
| 2016/0043384 A1* | 2/2016 | Zhamu | H01M 4/366 | 429/231.4 |
| 2016/0065169 A1* | 3/2016 | Rinaldi | H03H 3/02 | 250/338.3 |
| 2016/0091447 A1* | 3/2016 | Yu | G01N 27/125 | 73/31.06 |
| 2016/0116430 A1* | 4/2016 | Nauber | G01N 27/4045 | 205/780.5 |
| 2016/0123947 A1* | 5/2016 | Briman | G01N 27/129 | 422/90 |
| 2016/0161388 A1* | 6/2016 | Niedermayer | G01N 29/036 | 73/54.41 |
| 2016/0169824 A1* | 6/2016 | Shin | G01N 27/127 | 73/31.06 |
| 2016/0177387 A1* | 6/2016 | Roy | C12Q 2563/137 | 435/6.1 |
| 2016/0181868 A1* | 6/2016 | Casse | H01Q 1/248 | 307/104 |
| 2016/0185603 A1* | 6/2016 | Bozalina | B02C 17/20 | 252/71 |
| 2016/0195488 A1* | 7/2016 | Ensor | G01N 27/227 | 422/69 |
| 2016/0282312 A1* | 9/2016 | Cable | G01N 29/022 | |
| 2016/0290956 A1* | 10/2016 | Sato | H01L 29/78618 | |
| 2017/0096341 A1* | 4/2017 | Chen | C01B 32/184 | |
| 2017/0113935 A1* | 4/2017 | Pennington | B01J 19/129 | |
| 2017/0174520 A1* | 6/2017 | Walters | C01B 32/184 | |
| 2017/0181669 A1* | 6/2017 | Lin | A61B 5/145 | |
| 2017/0236726 A1* | 8/2017 | Jeong | H01L 21/02057 | 438/747 |
| 2017/0276634 A1* | 9/2017 | Saffell | G01N 33/0039 | |
| 2017/0315075 A1* | 11/2017 | Akinwande | G01N 27/125 | |
| 2017/0322094 A1* | 11/2017 | Kim | G06F 3/044 | |
| 2017/0330004 A1* | 11/2017 | Gibson | C08F 120/06 | |
| 2017/0350882 A1* | 12/2017 | Lin | A61B 5/6821 | |
| 2017/0356869 A1* | 12/2017 | Koenig | G01N 33/0027 | |
| 2018/0059080 A1* | 3/2018 | Jun | G01N 33/0013 | |
| 2018/0136157 A1* | 5/2018 | Harada | G01N 27/4146 | |
| 2018/0275088 A1* | 9/2018 | Huff | B01L 3/502715 | |
| 2019/0064143 A1* | 2/2019 | Haick | G01N 27/22 | |
| 2019/0072510 A1* | 3/2019 | Tai | H01L 51/0048 | |
| 2019/0277702 A1* | 9/2019 | Aleman | G01J 5/20 | |
| 2019/0312171 A1* | 10/2019 | Karabiyik | H01L 31/028 | |
| 2020/0080977 A1* | 3/2020 | Isobayashi | G01N 1/4005 | |
| 2020/0244243 A1* | 7/2020 | Cullinan | H03H 3/0073 | |

* cited by examiner

FIG. 3
(Prior Art)

| Family | Name |
|---|---|
| Metallocenes | Ferrocene |
| | Cobaltacene |
| | Ferrocenium |
| | Cp*2Fe(II) |
| Chelatases | Iron porphine |
| | Vitamin B12 |
| Coordination compounds | Ru(Bipy)3 |
| | dicyanobis(ethylenediamine)cadmium(II) |
| Organics | NADH |
| | Tetracyanoquinodimethane |
| | Tetramethyl-p-phenyldiamine |
| | Cyanocobalamin |
| | Tetrathiafulvalene |
| Polymers | TEMPO |
| | PTMA |
| | PVFCN |

FIG. 8

RESONANT GAS SENSOR

RELATED APPLICATIONS

This application is a Continuation of U.S. Ser. No. 16/239,423, filed on Jan. 3, 2019, now U.S. Pat. No. 10,502,705, which claims the benefit of U.S. Provisional Patent Application No. 62/613,716, filed on Jan. 4, 2018, and entitled "Volatiles Sensor"; which is hereby incorporated by reference for all purposes.

BACKGROUND

Chemical sensors operate by generating a signal in response to the presence of a particular analyte. Graphene-based sensors are one type of chemical sensor that have been increasing in development recently. FIG. 1 illustrates a plan view of a conventional graphene-based sensor for chemical vapor or gas sensing, illustrated as a chemiresistor 100. A sensing material 120 bridges two electrodes 110 and 111. When vapors pass through the sensing material 120 in parts per billion (ppb) range, a change in resistance of the graphene sensing material is observed and a resistance measurement 160 can be taken.

FIG. 2 is a perspective view of a conventional graphene-based sensor 200 configured as a field effect transistor (FET), where a first metal electrode 210 serves as the source, a second metal electrode 211 serves as the drain, and a functionalized graphene channel 220 forms the gate. The electrodes 210 and 211 and the channel 220 are mounted on a dielectric material 230. The sensor 200 shows that graphene-based chemical sensors can be configured as field effect transistors (FETs) to identify specific species and quantify the concentration of the species in a sample.

Figure 3:
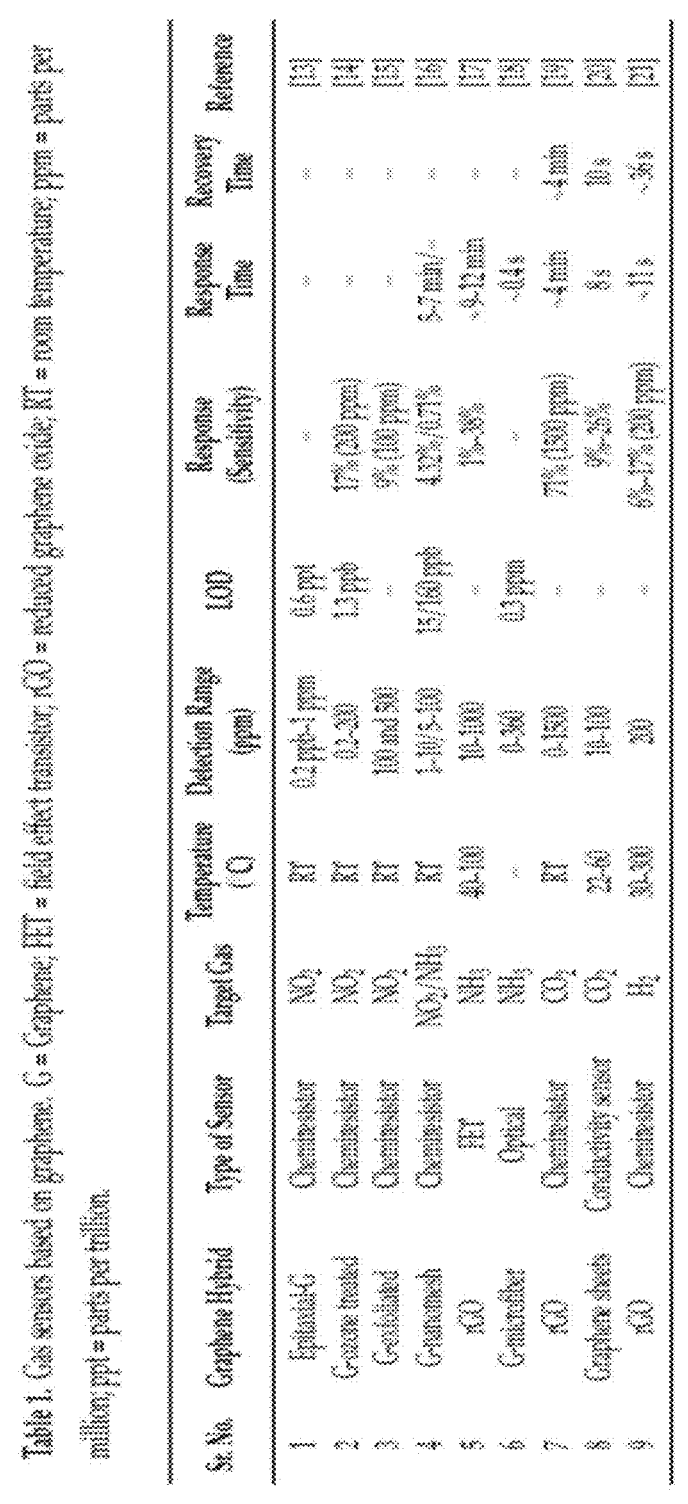

FIG. 3 is a table listing examples of conventional gas sensors based on graphene. Various graphene hybrids such as epitaxial-G, G-ozone treated, G-exfoliated, G-nanomesh, rGO, G-microfiber and graphene sheets can be used to make chemiresistors, FETs, optical sensors, and conductivity sensors. The table in FIG. 3 lists the target gases, temperatures, detection range, limit of detection (LOD), response sensitivity, response time, and recovery time for the various conventional graphene sensors.

Conventional gas sensors, however, require high power energy sources to sense low levels of chemistry, and the high cost of such equipment has made widespread adoption impractical for many applications. Many conventional systems also rely on adding energy (e.g., using elevated temperatures) to drive the sensing reactions within the sensor and improve the sensitivity. The equipment required for conventional gas sensors is also not readily miniaturized, which limits their use in mobile applications.

SUMMARY

In some embodiments, a method for detecting an analyte comprises providing a first carbon-based material comprising reactive chemistry additives, providing conductive electrodes connected to the first carbon-based material, exposing the first carbon-based material to an analyte material, applying a plurality of alternating currents having a range of frequencies across the conductive electrodes, and measuring the complex impedance of the first carbon-based material using the plurality of alternating currents. In some embodiments of the above method, the providing the first carbon-based material comprises using a microwave plasma to produce carbon particles, and printing the carbon particles to form the first carbon-based material. In some cases, the reactive chemistry additives are tuned to the analyte materials.

In some embodiments, a sensor for detecting an analyte comprises a flexible substrate, a resonant gas sensor circuit, and a microprocessor arranged on the flexible substrate and electrically coupled to a second terminal of the transducer and to the ground electrode. The resonant gas sensor circuit can comprise a transducer arranged on the flexible substrate, a sensing material arranged on the flexible substrate, wherein the sensing material is coupled to the transducer, and comprises a first particulate carbon and a reactive chemistry additive, and a ground electrode electrically coupled to a first terminal of the transducer. The microprocessor can comprise an alternating current (AC) source configured to supply a plurality of AC signals to the transducer, the plurality of AC signals comprising a range of frequencies, and a detection circuit that measures a plurality of AC signals reflected from the transducer. The sensing material can comprise a plurality of carbon aggregates each comprising a plurality of carbon nanoparticles. Each carbon nanoparticle can comprise graphene, the graphene in the plurality of carbon nanoparticles comprises up to 15 layers, a percentage of carbon to other elements, except hydrogen, in the carbon aggregates is greater than 99%, a median size of the carbon aggregates comprising the carbon nanoparticles is from 0.1 microns to 50 microns, a surface area of the carbon aggregates is from 10 $m^2/g$ to 300 $m^2/g$, when measured via a Brunauer-Emmett-Teller (BET) method with nitrogen as the adsorbate, and the carbon aggregates, when compressed, have an electrical conductivity from 500 S/m to 20,000 S/m.

BRIEF DESCRIPTION OF DRAWINGS

FIG. 3 (Prior Art) is a table listing examples of conventional gas sensors based on graphene.

FIG. 8 is a table that lists examples of possible redox mediators that may be used, in accordance with some embodiments.

DETAILED DESCRIPTION

Figure 1:
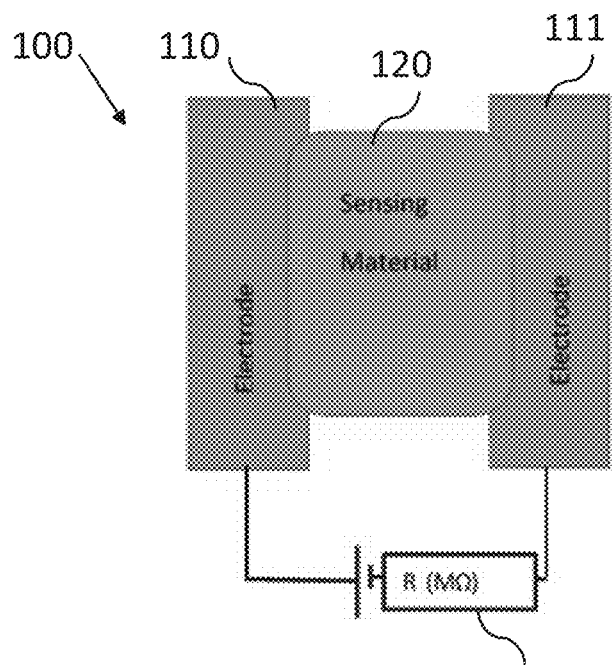
FIG. 1 (Prior Art) is a plan view of a conventional graphene-based sensor for chemical vapor or gas sensing.
Figure 2:
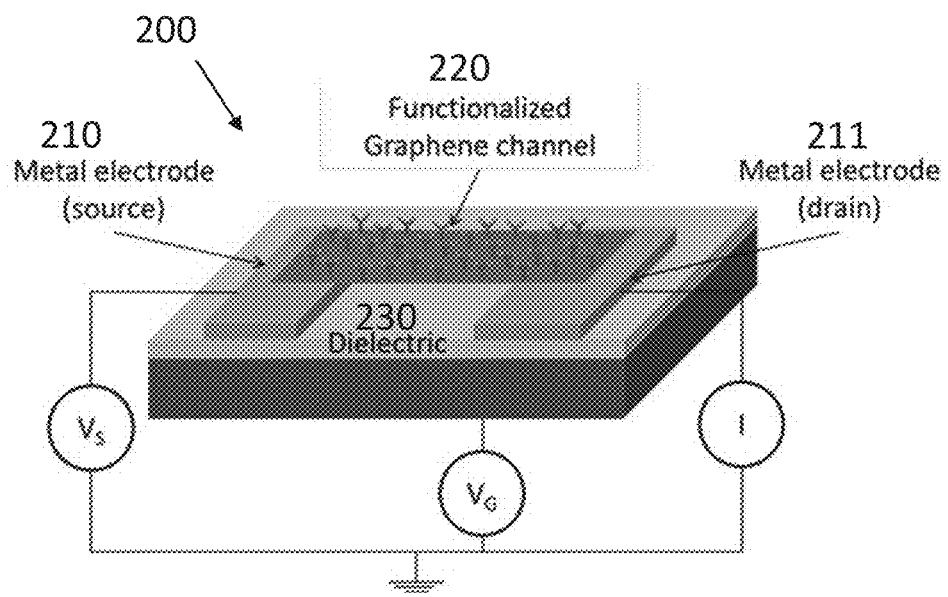
FIG. 2 (Prior Art) is a perspective view of a conventional graphene-based sensor 200 configured as a field effect transistor (FET).

In the present embodiments, devices incorporating carbon-based materials and material composites are described that can be used for chemical sensing of analytes (e.g., one or more volatile gases or vapors). In some embodiments, a gas sensor contains a reactive chemistry additive that is incorporated into a sensing material. Upon exposure to an analyte, the reactive chemistry additive reacts with the analyte and changes the electrical properties of the sensing material. The electrical properties of the sensing material are interrogated by circuitry in the gas sensor, and the change in electrical properties due to analyte exposure can be detected. The properties of the present carbon-based materials coupled with the device architectures described herein can improve the sensitivity and power consumption for such gas sensors used to detect an analyte. Additionally, the present embodiments are compatible with miniature gas sensors, which enables a myriad of applications not available to non-portable gas sensors.

The present gas sensors used for detecting chemical substances have many applications. Some non-limiting examples include environmental monitoring (e.g., indoor air quality, water testing, waste water treatment, chemical manufacturing, and total ion counts), industrial safety (e.g., toxic compound detection), food and beverage industry applications (e.g., monitoring of food fermentation process, freshness/ripeness and spoilage), defense and first response applications (e.g., chemical warfare agents, chemical threat agents, and explosives), and biomedical applications (e.g., infection monitoring, antioxidant level monitoring, and biospecimen monitoring).

In some embodiments, analytes (e.g., volatile gases or vapors) are sensed using impedance spectroscopy-based electrochemical sensors. The present embodiments use low cost materials and methods for printing electrical components on backing materials (e.g., labels, smart cards, and packaging materials) which can be integrated with other hardware components on a substrate (e.g., a flexible substrate) to create electro-active devices.

In some embodiments, sensors for detecting chemical substances in a vapor phase are made using printed, carbon-based electrical components. In some embodiments, the carbon materials are tailored to sense a specific chemical targeted by a particular sensor. The present sensors can operate under low power requirements and at room temperature, while providing a high sensitivity to detect airborne chemicals. The printed sensors can be configured as, for example, labels that can be affixed to containers such as shipping boxes, to monitor the contents within the container. In some embodiments, more than one sensor can be printed on a single label, where each sensor is configured to detect a different chemical. In this manner, the combination of the chemicals detected by the different sensors on the label can indicate the presence of a compound that is unstable or difficult to detect.

Sensors for detecting target chemical moieties in some embodiments include a first electrode made of a first conductive ink, the first conductive ink comprising a first carbon allotrope; a second electrode made of a second conductive ink, the second conductive ink comprising a second carbon allotrope; and a substrate on which the first electrode, the second electrode, and the sensing material are printed. At least one of the first electrode, the second electrode, or the sensing material can also comprise a redox mediator. In some embodiments, a printed chemiluminescent sensor is made of a composite material that includes a luminescent dye tethered to a graphene-based material.

In some embodiments, the use of unique carbon materials and carbon material composites made by novel microwave plasma and thermal cracking equipment and methods make it possible in the present embodiments to provide low power solutions to many devices and applications of an electronic nature. For example, sensors, electronics and displays can be printed with the present materials, realizing many different types of application scenarios. Energy harvesting technologies are also realized through the use of these materials to provide viable power to microprocessor devices in real world applications with sophisticated microprocessor controls.

Carbon Materials for Gas Sensors

The present gas sensors for detecting analytes (e.g., volatile compounds) can incorporate unique carbon materials (e.g., produced using microwave plasma or thermal cracking equipment), as described further below.

In some embodiments, 3-dimensionally structured (e.g., microporous, mesoporous and/or hierarchical structures) carbon (e.g., graphene) particles are used in gas sensors. The porosity, surface area, and surface philicity/polarity of the carbon particles can be tuned to change the properties of the particles (e.g., their complex impedance). The carbon acts as an electrically conductive scaffold supporting a second phase of material (e.g., a dielectric polymer), such that the properties of the combined particle (e.g., the electrical resistivity and/or the complex impedance) can change when exposed to one or more analytes. The properties of the carbon and the second phase of material can each be tuned to produce a combined material that is electrically conducting, molecular sieving, and an efficient gas adsorption framework, and is capable of detecting a wide range of analytes (e.g., volatile gases or vapors) for numerous applications. In some embodiments, the particulate carbon described herein is used to form frequency selective materials, which can be used in resonant circuits within the present gas sensors.

In some embodiments, the carbon particles are formed into a film using a polymer as a binder. In some cases, the surface area and porosity of the carbon particles, and the polymer binder to carbon particle ratio can be tuned to provide molecular sieving (i.e., effecting rate of analyte (e.g., volatile organic compound) diffusion (or mass transport) and separation) for enhanced molecular size and shape selectivity.

In some embodiments, the carbon (e.g., graphene) surfaces can be modified (e.g., functionalized) to affect adsorption behavior and the dielectric properties of the material. Such surface modification of the sensing material can increase the dielectric changes (from both the graphene and polymer materials) upon interaction with an analyte and therefore improve the sensitivity and analyte selectivity of the sensor.

In some embodiments, the carbon surface can be functionalized to tune the philicity/polar nature of the surface and as a result, a sensing material can be created with an engineered response to humidity. For example, sensors can be fabricated with non-wetting hydrophobic graphene surfaces to minimize effect of moisture/humidity. Alternatively, sensors with a 2-element sensor array containing hydrophilic and hydrophobic specific graphene detectors (e.g., multiples of each type of sensor in an array configuration) can provide greater sensitivity and selectivity by accounting for (e.g., subtracting out) background effects from humidity. This approach can be extended to arrays of sensors with differently tuned sensing materials to enable various materials (e.g., impurities) to be accounted for through signal processing methods (e.g., high/low response of a 2-level (or higher order) detector array).

In some embodiments, the unique carbon material is a particulate carbon with improved properties compared to conventional carbon materials. For example, the particulate carbon can have high compositional purity, high electrical conductivity, and a high surface area compared to conventional carbon materials. The high surface area, for example, provides a large concentration of gas sensing sites (e.g., bonding sites for reactive chemistry additives used to detect target chemical species), which improves the lower detection limit of the sensor. Additionally, the high electrical conductivity is beneficial to gas sensors because less power is lost due to parasitic resistive heating of the electrical components of the gas sensors (e.g., the electrodes, or the sensing material of the gas sensors).

In some embodiments, the particulate carbon also has a structure that is beneficial for gas sensor performance, such as small pore sizes and/or a mesoporous structure. In some cases, a mesoporous structure can be characterized by a structure with a wide distribution of pore sizes (e.g., with a multimodal distribution of pore sizes). For example, a multimodal distribution of pore sizes can be indicative of structures with high surface areas and a large quantity of small pores that are efficiently connected to a substrate supporting the material and/or current collector via material in the structure with larger feature sizes (i.e., that provide more conductive pathways through the structure). Some non-limiting examples of such structures are fractal structures, dendritic structures, branching structures, and aggregate structures with different sized interconnected channels (e.g., composed of pores and/or particles that are roughly cylindrical and/or spherical). A mesoporous structure can be particularly beneficial to gas sensors. Not to be limited by theory, the mesoporous structure can provide a framework with low resistance electrical pathways through the material, while simultaneously providing high surface area structures beneficial to the detection limit.

In some embodiments, the particulate carbon materials used in the gas sensors described herein are produced using microwave plasma reactors and methods, such as any appropriate microwave reactor and/or method described in U.S. Pat. No. 9,812,295, entitled "Microwave Chemical Processing," or in U.S. Pat. No. 9,767,992, entitled "Microwave Chemical Processing Reactor," which are assigned to the same assignee as the present application, and are incorporated herein by reference as if fully set forth herein for all purposes. Additional information and embodiments for microwave plasma gas processing system methods and apparatuses to produce the carbon nanoparticles and aggregates described herein are also described in the related U.S. Patents and Patent Applications mentioned in this disclosure.

In some embodiments, the gas sensors described herein contains one or more particulate carbon materials. In some embodiments, the particulate carbon materials used in the gas sensors described herein described herein are described in U.S. Pat. No. 9,997,334, entitled "Seedless Particles with Carbon Allotropes," which is assigned to the same assignee as the present application, and is incorporated herein by reference as if fully set forth herein for all purposes. In some embodiments, the particulate carbon materials contain graphene-based carbon materials that comprise a plurality of carbon aggregates, each carbon aggregate having a plurality of carbon nanoparticles, each carbon nanoparticle including graphene, optionally including multi-walled spherical fullerenes, and optionally with no seed particles (i.e., with no nucleation particle). In some cases, the particulate carbon materials are also produced without using a catalyst. The graphene in the graphene-based carbon material has up to 15 layers. A ratio (i.e., percentage) of carbon to other elements, except hydrogen, in the carbon aggregates is greater than 99%. A median size of the carbon aggregates is from 1 micron to 50 microns, or from 0.1 microns to 50 microns. A surface area of the carbon aggregates is at least 10 $m^2/g$, or is at least 50 $m^2/g$, or is from 10 $m^2/g$ to 300 $m^2/g$, or is from 50 $m^2/g$ to 300 $m^2/g$, when measured using a Brunauer-Emmett-Teller (BET) method with nitrogen as the adsorbate. The carbon aggregates, when compressed, have an electrical conductivity greater than 500 S/m, or greater than 5000 S/m, or from 500 S/m to 20,000 S/m.

In some embodiments, the particulate carbon materials used in the gas sensors described herein are described in U.S. Pat. No. 9,862,606 entitled "Carbon Allotropes," which is assigned to the same assignee as the present application, and is incorporated herein by reference as if fully set forth herein for all purposes. In some embodiments, the particulate carbon materials contain carbon nanoparticles comprising at least two connected multi-walled spherical fullerenes, and layers of graphene coating the connected multi-walled spherical fullerenes. Additionally, the carbon allotropes within the carbon nanoparticles can be well ordered. For example, a Raman spectrum of the carbon nanoparticle using 532 nm incident light can have a first Raman peak at approximately 1350 $cm^{-1}$ and a second Raman peak at approximately 1580 $cm^{-1}$, and a ratio of an intensity of the first Raman peak to an intensity of the second Raman peak is from 0.9 to 1.1. In some cases, the atomic ratio of graphene to multi-walled spherical fullerenes is from 10% to 80% within the carbon nanoparticles.

In some embodiments, the particulate carbon materials described herein are produced using thermal cracking apparatuses and methods, such as any appropriate thermal apparatus and/or method described in U.S. Pat. No. 9,862,602, entitled "Cracking of a Process Gas," which is assigned to the same assignee as the present application, and is incorporated herein by reference as if fully set forth herein for all purposes. Additional information and embodiments for thermal cracking methods and apparatuses to produce the carbon nanoparticles and aggregates described herein are also described in the related U.S. Patents and Patent Applications mentioned in this disclosure.

In some embodiments, the particulate carbon used in the present gas sensors contains more than one type of carbon allotrope. For example, the particulate carbon can contain graphene, spherical fullerenes, carbon nanotubes, amorphous carbon, and/or other carbon allotropes. Some of these carbon allotropes are further described in the related U.S. Patents and Patent Applications mentioned in this disclosure. Additionally, the different carbon allotropes in the particulate carbon can have different morphologies, such as mixtures of low and high aspect ratios, low and high surface areas, and/or mesoporous and non-mesoporous structures. The use of particulate carbon with combinations of different allotropes (and in some cases different morphologies) can enhance the electrical and mechanical properties of different components of the present gas sensors (e.g., electrodes, or sensing materials). The mass ratio of a first carbon allotrope (e.g., with high electrical conductivity and/or a mesoporous structure) to a second carbon allotrope (e.g., a long chain carbon allotrope) in the particulate carbon can be from 70:30 to 99:1, or from 80:20 to 90:10, or from 85:15 to 95:5, or is about 85:15, or is about 90:10, or is about 95:5. For example, mesoporous carbon allotropes in the particulate carbon can provide high surface area and/or high electrical conductivity, and the addition of long chain (i.e., high aspect ratio) carbon allotropes in the particulate carbon can improve the mechanical strength, adhesion and/or durability of the present gas sensor components.

In some embodiments, the particulate carbon used in the present gas sensors contains particles containing graphene (e.g., with one or more of the properties described herein), and particles containing long chain carbon allotropes (e.g., spherical fullerenes connected in a string-like arrangement, or carbon nanotube bundles). In some embodiments, the long chain carbon allotropes have aspect ratios greater than 10:1, or from 10:1 to 100:1, or about 10:1, or about 20:1, or about 50:1, or about 100:1. In some embodiments, the long chain carbon allotropes have dimensions from 50 nm to 200 nm wide by up to 10 microns in length, or from 10 nm to 200 nm wide by from 2 microns to 10 microns in length. Additional particles containing long chain carbon allotropes are described in the related U.S. Patents and Patent Applications mentioned in this disclosure. The mass ratio of a graphene-containing carbon allotrope to a long chain carbon allotrope in the particulate carbon can be about 85:15, or about 90:10, or about 95:5. In some embodiments, the long chain carbon allotropes can interlock with other conductive (and in some cases structured, or mesoporous) carbon allotropes in the particulate carbon and can form an interlocked hybrid composite allotrope gas sensor component (e.g., electrode or sensing material) with improved mechanical properties compared to components without long chain carbon allotropes. In some embodiments, the addition of long chain (e.g., fibrous like) carbon increases the medium range (e.g., 1 micron to 10 microns) conductivity, and the distribution of the other carbon allotrope (e.g., prevents agglomeration of the other carbon allotrope, such as mesoporous graphene particles), while improving mechanical stability. Furthermore, the addition of long chain carbon allotropes can provide additional porosity around the carbon chain, which increases ion conductivity and mobility in the gas sensor component. In one embodiment, these long chain fibers enable reduced calendaring pressure during fabrication (leading to components with increased local voidage or porosity), while maintaining the same (or better) mechanical stability (i.e., tolerance to delamination and/or cracking) as components without long chain carbons that are calendared at higher pressures. Reduced calendaring pressure can be advantageous because the higher porosity achieved using a lower pressure leads to increase ion conductivity and/or mobility. Additionally, in some embodiments, the addition of long chain carbon (e.g., fibers) can improve the elongation/strain tolerance over conventional slurry cast components. In some cases, the elongation/strain tolerance (e.g., the maximum strain to failure, or the amount of performance degradation for a given strain) can be increased by as much as 50% over conventional slurry cast components. In some embodiments, the addition of long chain carbon allotropes to the particulate carbon in a gas sensor component enables the use of less binder, or the elimination of the binder, in the component.

In a non-limiting example, a mechanically robust, hybrid composite electrode or sensing material film can contain particulate carbon with a combination of lower density (e.g., mesoporous), hierarchical graphene-containing particles (e.g., with particle sizes from 15 to 40 microns in diameter) and higher density particles containing long chains of connected spherical fullerenes (e.g., with sizes 50 to 200 nm wide by up to 10 microns in length). The mass ratio of graphene carbon allotropes to the long chain allotropes in this example is about 85:15. The particulate carbon in this example has high electrical conductivity (due to the high electrical conductivity of the graphene and/or spherical fullerenes), and the long chain allotropes provide mechanical reinforcement.

In conventional films (or patterned traces) containing conductive and/or active materials particles, a binder is often used to improve the mechanical properties. In some embodiments, the present gas sensor components are mechanically reinforced by long chain carbon allotropes, which enables the reduction or the elimination of a binder in the components. For example, an interlocked hybrid composite allotrope film (or patterned trace) containing mesoporous graphene and long chain carbon allotropes can be formed with suitable mechanical properties without the use of a binder. Such components with no binder can also be free-standing components (i.e., are mechanically stable without being attached to a substrate).

In some embodiments, an interlocked hybrid composite allotrope gas sensor component can be formed by sintering the particulate carbon after component formation (e.g., after printing, or slurry casting). This process can be used to consolidate and strengthen the composite component structure.

In a non-limiting example, carbon particles and aggregates containing graphite and graphene were generated using a microwave plasma reactor system, described in U.S. Pat. No. 9,767,992, entitled "Microwave Chemical Processing Reactor." The microwave plasma reactor in this example had a main body made from stainless steel with a quartz inner wall material. However, the quartz inner wall material is not needed in all cases, and similar carbon materials can be produced in reactors without quartz in or adjacent to the reaction zone. In some embodiments, it is beneficial to produce the particulate carbon in a reactor that does not have quartz in or adjacent to the reaction zone, because materials, such as oxygen, can decompose out of the quartz and become incorporated as unwanted impurities in the produced carbon materials. The reaction zone volume was approximately 45 cm$^3$. The precursor material was methane and was optionally mixed with a supply gas (e.g., argon). The flow rate of methane was from 1 to 20 L/min, the flow rate of the supply gas was from 0 to 70 L/min. With those flow rates and the tool geometry, the residence time of the gas in the reaction chamber was from approximately 0.001 second to approximately 2.0 seconds, and the carbon particle production rate was from approximately 0.1 g/hr to approximately 15 g/hr. After the aggregates were synthesized and collected, they were post-processed by annealing at a temperature from 1000 to 2200° C. in an inert atmosphere for a duration of approximately 60 to approximately 600 minutes.

The particles produced in this example contained carbon aggregates containing a plurality of carbon nanoparticles, where each carbon nanoparticle contained graphite and graphene and did not contain seed particles. The particles in this example had a ratio of carbon to other elements (other than hydrogen) of approximately 99.97% or greater.

Figure 4:
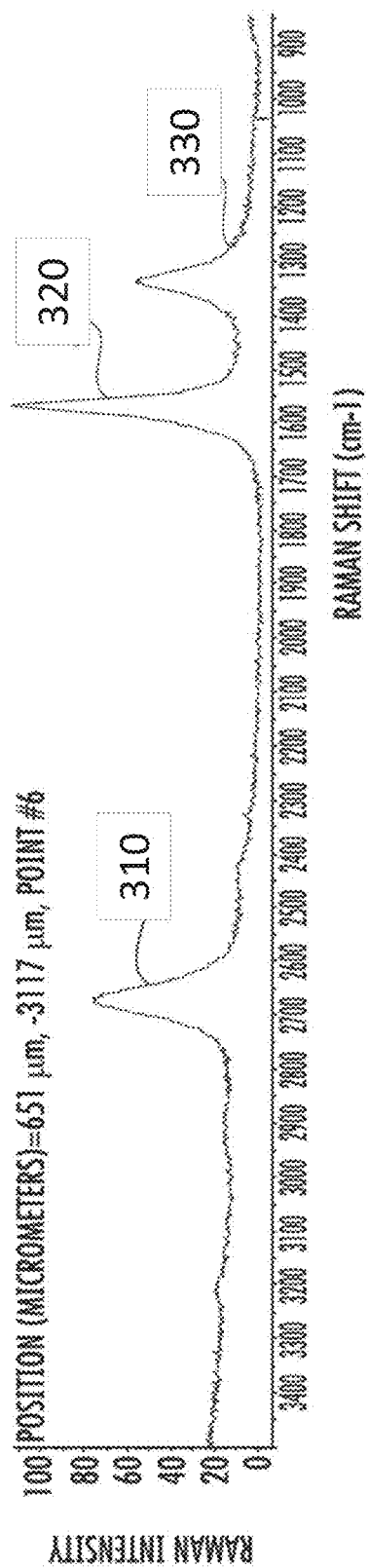
FIG. 4 shows a Raman spectrum from particulate carbon containing graphene, in accordance with some embodiments.

FIG. 4 shows a Raman spectrum of the particulate carbon of this example, taken using 532 nm incident light. The particles in FIG. 4 were produced using precursors containing argon. The spectrum has a 2D-mode peak 310 at approximately 2690 cm$^{-1}$, a G-mode peak 320 at approximately 1580 cm$^{-1}$, and a D-mode peak 330 at approximately 1350 cm$^{-1}$, and the 2D/G intensity ratio is greater than 0.5. The 2D/G intensity ratio for the particles produced in FIG. 4 is approximately 0.7.

The size of the aggregates in this example have a median of approximately 11.2 microns as-synthesized, and approximately 11.6 microns after annealing. The size distribution of the as-synthesized aggregates had a 10$^{th}$ percentile of approximately 2.7 microns, and a 90$^{th}$ percentile of approximately 18.3 microns. The annealed aggregates size distribution had a 10$^{th}$ percentile of approximately 4.2 microns, and a 90$^{th}$ percentile of approximately 25.5 microns.

The electrical conductivity of the aggregates was measured after being compressed into pellets. The as-synthesized (i.e., before annealing) material had a conductivity of 800 S/m when compressed using 2000 psi of pressure, and a conductivity of 1200 S/m when compressed using 12,000 psi of pressure. The annealed material had a conductivity of 1600 S/m when compressed using 2000 psi of pressure, and a conductivity of 3600 S/m when compressed using 12,000 psi of pressure.

Figure 5A:
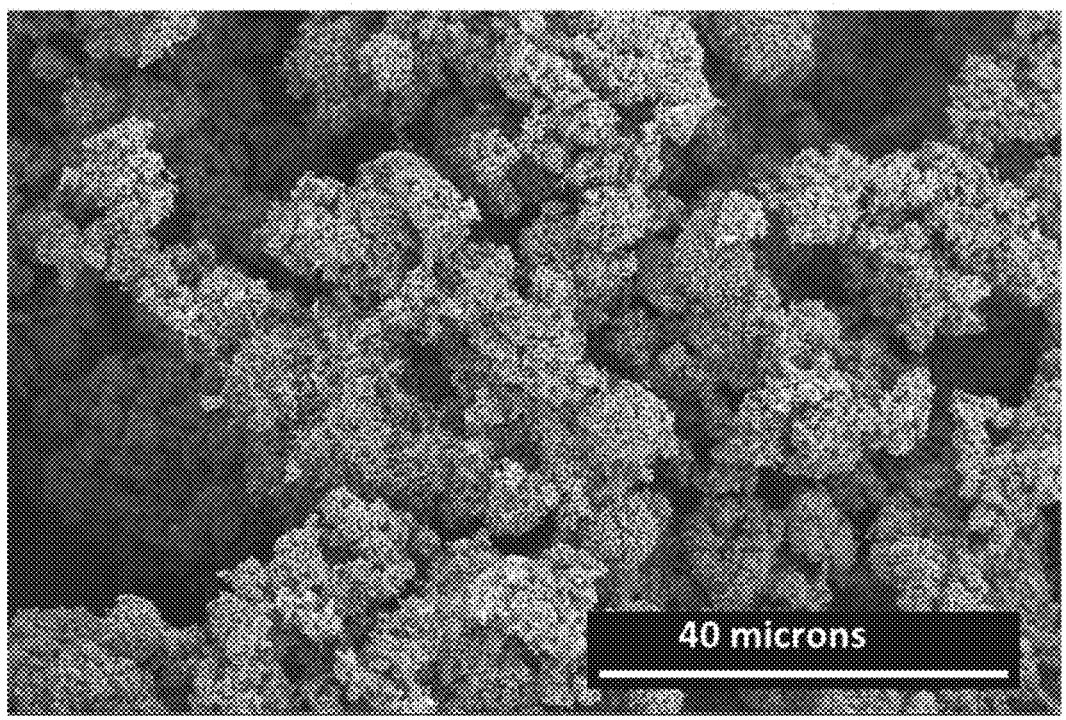
FIGS. 5A and 5B show scanning electron microscope (SEM) images from particulate carbon containing graphene, in accordance with some embodiments.
Figure 5B:
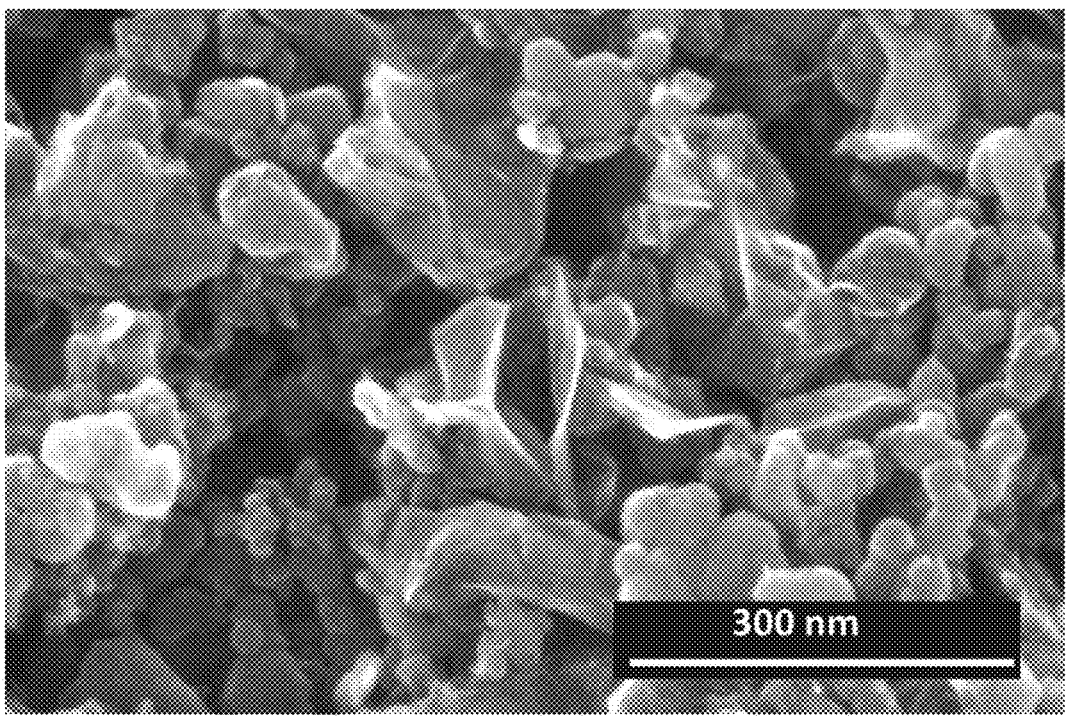
Figure 6A:
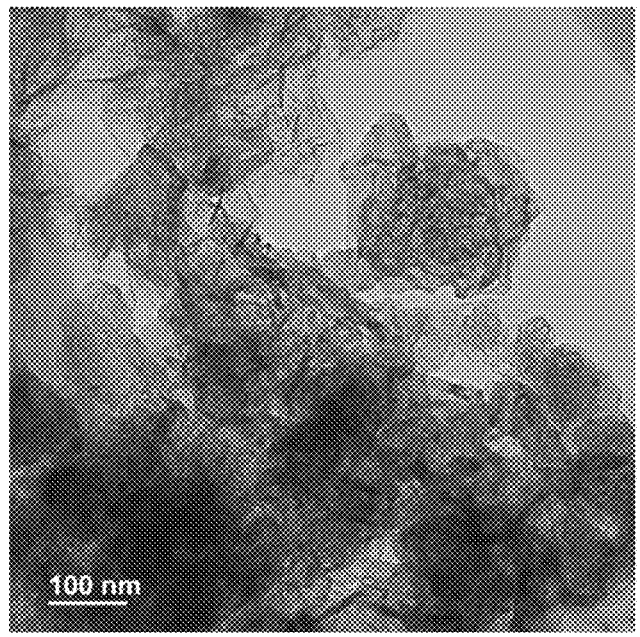
FIGS. 6A and 6B show transmission electron microscope (TEM) images from particulate carbon containing graphene, in accordance with some embodiments.
Figure 6B:
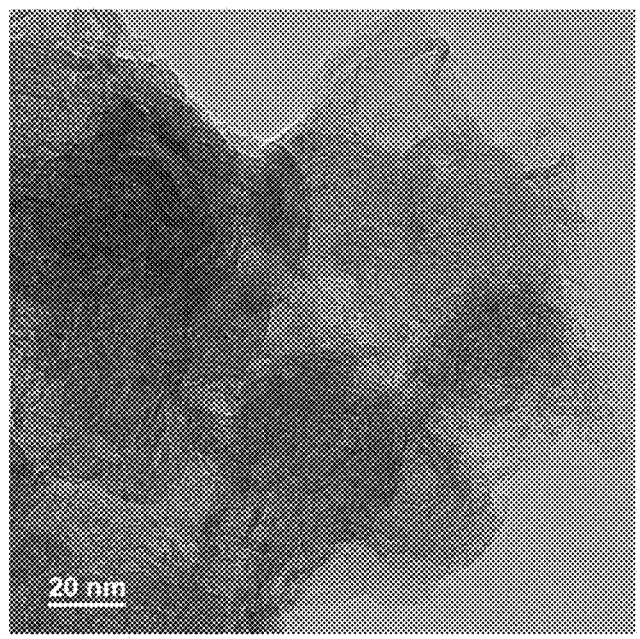

FIGS. 5A and 5B show SEM images, and FIGS. 6A and 6B show TEM images, of the carbon aggregates of the particulate carbon of this example showing graphite and graphene allotropes. The layered graphene is clearly shown within the distortion (wrinkles) of the carbon. The 3D structure of the carbon allotropes is also visible. The carbon allotropes in this example have a 3D structure with a hierarchical mesoporous, few layer, graphene structure with a specific edge-to-basal plane ratio. In some embodiments, the edge-to-basal plane ratio for the graphene in the present particulate carbon is about 1:10, or about 1:100, or from 1:10 to 1:100.

The surface area of the aggregates in this example were measured using the nitrogen BET method and the density functional theory (DFT) method. The surface area of the aggregates as determined by the BET method was approximately 85.9 m$^2$/g. The surface area of the aggregates as determined by the DFT method was approximately 93.5 m$^2$/g.

In contrast to conventionally produced carbon materials, the microwave plasma reactor produced carbon particles and aggregates in this example contained graphite and graphene had high purity, high electrical conductivities, and large surface areas. Additionally, these particles had Raman signatures indicating a high degree of order, and contained no seed particles.

In some embodiments, the particulate carbon in the present gas sensors contains doped carbon materials (e.g., carbon doped with H, O, N, S, Li, Cl, F, Si, Se, Sb, Sn, Ga, As, and/or other metals), undoped carbon materials, or combinations thereof. Doped carbon can also include carbon with a matrix allotrope doped with carbon atoms (not in the matrix structure) and/or doped with other types of carbon allotropes. Doped carbon materials can also be doped with functional groups, such as amine (NH$_3$) groups. In some embodiments, doped carbon materials are formed using a dopant material, where the dopant material is introduced within a gas, liquid, or colloidal dispersion and fed into a reactor that is used to produce the doped particulate carbon. For example, dopant materials can be combined with a hydrocarbon precursor material and cracked in a reactor (e.g., a microwave plasma reactor or a thermal reactor) to produce a doped particulate carbon.

In some embodiments, the particulate carbon in the present gas sensors contains nano-mixed particulate carbon. In some embodiments, the surface area, structure, and/or surface activity of the present particulate carbon materials are tuned by nano-mixing the carbon particles within the carbon materials with particles of other materials. In some embodiments, particles of nano-mix additive materials can be beneficially integrated with particles of the graphene-based carbon on a particle level, which shall be referred to as nano-mixing in this disclosure. The average diameter of the particles of the nano-mix additive material and the graphene-based carbon materials in the nano-mixed particulate carbon can be from 1 nm to 1 micron, or from 1 nm to 500 nm, or from 1 nm to 100 nm, or can be as small as 0.1 nm In some embodiments, the nano-mix additive material and the graphene-based carbon material are chemically bound, or are physically bound, together in the nano-mixed particulate carbon. In some embodiments, the nano-mixing involves introducing nano-mix additives during particulate formation (e.g., during a hydrocarbon cracking process in a microwave plasma reactor or in a thermal reactor) such that the nano-mix additive material is integrated into the graphene-based carbon material as the carbon material is produced, rather than combining a carbon raw material with an additive in a later process as in certain conventional methods. In some embodiments, the nano-mix additive material can be introduced as a gas, liquid, or colloidal dispersion into a reactor that is used to produce the nano-mixed particulate carbon. As an example, silicon can be input into a reactor along with a hydrocarbon process gas (or other carbon-containing process material such as a liquid alcohol) to produce silicon nano-mixed with graphene, graphene-based carbon materials, and/or other carbon allotropes. In other examples, the resulting nano-mixed particulate carbon of the present embodiments can contain particles of O, S, Li$_x$S$_y$ (where x=0-2 and y=1-8), Si, Li$_{22}$Si$_5$, Li$_{22-x}$Si$_{5-y}$ (where x=0-21.9, and y=1-4.9), and Li$_{22-x}$Si$_{5-y-z}$M$_z$ (where x=0-21.9, y=1-4.9, z=1-4.9. and M is S, Se, Sb, Sn, Ga, or As), and/or other metals.

In some embodiments, the particulate carbon to be used in the present gas sensors are produced and collected, and no post-processing is done. In other embodiments, the particulate carbon is produced and collected, and some post-processing is done. Some examples of post-processing include mechanical processing, such as ball milling, grinding, attrition milling, micro-fluidizing, jet milling, and other techniques to reduce the particle size without damaging the carbon allotropes contained within. Some examples of post-processing include exfoliation processes such as shear mixing, chemical etching, oxidizing (e.g., Hummer method), thermal annealing, doping by adding elements during annealing (e.g., O, S, Li, Si, Se, Sb, Sn, Ga, As, and/or other metals), steaming, filtering, and lypolizing, among others.

Some examples of post-processing include sintering processes such as SPS (Spark Plasma Sintering, i.e., Direct Current Sintering), Microwave, and UV (Ultra-Violet), which can be conducted at high pressure and temperature in an inert gas. In some embodiments, multiple post-processing methods can be used together or in series. In some embodiments, the post-processing can produce the functionalized carbon nanoparticles or aggregates described herein.

The particulate carbon described herein can be combined with a second phase of material to create composite films. These composite films can be fabricated utilizing different methods to create specific detector responses.

In an example, solid carbon particles (e.g., particle size from 0.3 microns to 40 microns) and polymer beads (e.g., ball mixed for size reduction and improved aggregation) can be mixed in a ratio of 90:10 respectively (or in ratios from 95:10 to 5:95). This mixture can then be cast onto a substrate (e.g., one containing pre-fabricated electrodes, or an antenna platform), and then treated (e.g., using a low temperature, post treatment in an inert gas oven, a reactive gas oven, or a vacuum oven).

In another example, the mixing of the solid carbon particles and polymer beads described in the example above can be further combined with a solvent to form an ink, which can then be deposited onto a substrate (e.g., cast using doctor blade, or printed). After deposition, the film can then be treated at a low temperature to remove the solvent and consolidate the film.

In another example, particulate carbon can be encapsulated with a polymer to form colloidal core-shell structures that can be printed onto antenna platform using various techniques including inkjet printing, aerosol spray coating, spin coating and roll coating.

In another example, the particulate carbon can be combined with a soluble polymer to form jettable inks for printing. In such applications, conductive binders, such as silver flakes/particles, can also be added to tune the dielectric properties (e.g., at particle-particle contact points).

Electrochemical Sensors

Figure 7:
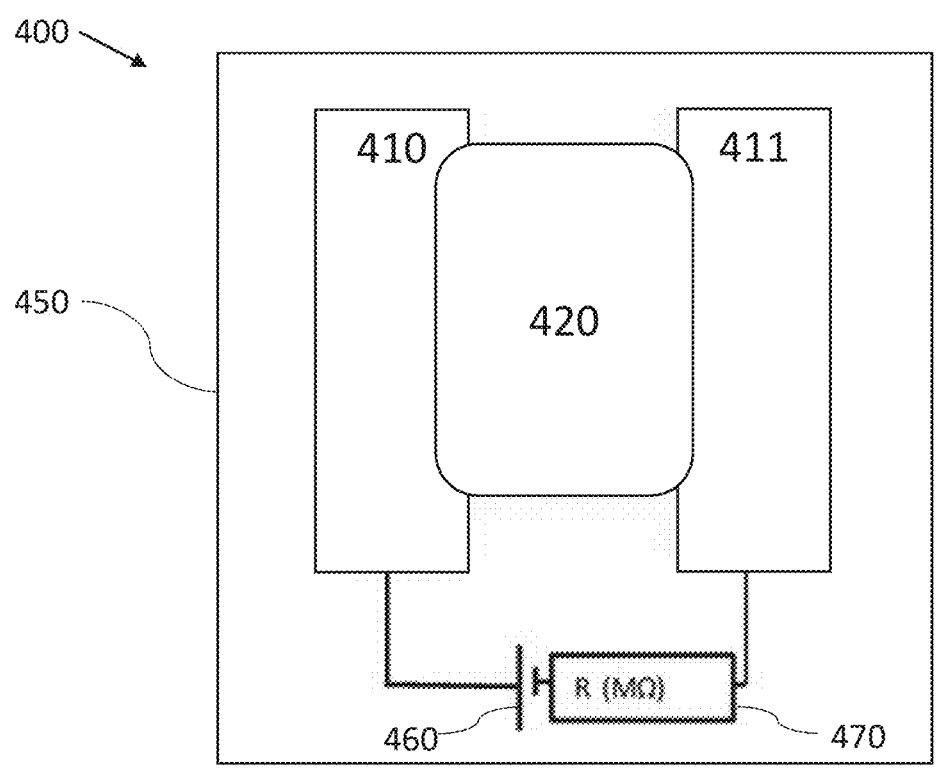
FIG. 7 is a plan view schematic of an electrochemical gas sensor, in accordance with some embodiments.

FIG. 7 is a plan view schematic of an electrochemical gas sensor 400, in accordance with some embodiments. The gas sensor 400 has a circuit containing a first electrode 410 printed from a conductive ink, a second electrode 411 printed from a conductive ink, a non-volatile electrolyte 420 that electrically couples the first electrode 410 to the second electrode 411, a signal generator 460 (shown as a voltage source), and a measurement (or detection) circuit element 470 (shown as a mega-Ohm resistance measurement in the figure, but could also be a capacitance, impedance or other electrical measurement in other embodiments). The presence of a target chemical produces a detectable signal between the two electrodes 410 and 411. For example, the change in the resistance of the circuit, the capacitance of the circuit, and/or the impedance of the circuit can be used as a detection signal. One of the electrodes 410 or 411 serves as the sensing electrode, and the other is the counter electrode. In some embodiments, one or both of the electrodes 410 and 411 contain particulate carbon (e.g., the particulate carbon described herein), silver particles, metal particles, conductive oxide particles (e.g., indium tin oxide and/or fluorine-doped tin oxide particles), or other conductive particulate materials (including any aspect ratio particulates, such as those shaped as spheroids, rods, and wires). In other embodiments, one or both of the electrodes 410 and 411 contain carbon allotropes such as, but not limited to, graphene, graphenes (graphene-based materials), graphene oxide, reduced graphene oxide, graphite oxide, graphite intercalation compounds, graphite, graphane, carbon nano-onions, diamond, p-type diamond, n-type diamond, glassy carbon, amorphous carbon, activated carbon, carbon black and/or carbon nano-tubes. The carbon materials in the first electrode 410 may be the same as or different from the carbon materials in the second electrode 411. In one embodiment, the first electrode 410 includes a high surface area, highly conductive carbon allotrope combined with a redox mediator such as from the class of metallocenes (e.g., ferrocene), while the second electrode 411 includes a conductive ink with a low surface area carbon allotrope with no redox mediator. In various embodiments, the first electrode 410, second electrode 411, and electrolyte 420 are all printed on a substrate 450, such as by ink-jet printing. In some embodiments, the substrate 450 is a rigid or flexible material, such as paper, such as paper used in a label material. Some other non-limiting examples of substrate materials are polymers (e.g., polyethylene terephthalate, or polypropylene), and cardboard. One benefit of the present gas sensors is that they can be printed on many different substrates, in accordance with some embodiments.

In some embodiments, the electrolyte 420 can be ink-jet printed and contain materials such as polymer electrolytes, ceramics, or monomers that solidify into a suitable solid electrolyte. Examples of liquid electrolyte materials include ionic liquids, such as 1-butyl-3-methylimidazolium bis(trifluoromethylsulfonyl)imide, 1-butyl-3-methylimidazolium hexafluorophosphate, 1-butyl-3-methylimidazolium tetrafluoroborate, 1-hexyl-3-methylimidazolium tris(pentafluoroethyl)trifluorophosphate, 1-butyl-1-methylpyrrolidinium bis(trifluoromethylsulfonyl)imide, ethylammonium nitrate, and tetrabutylmethylammonium bis(trifluoromethylsulfonyl)imide. Ionic liquid monomers with acrylate functional groups can be in-situ polymerized to make polymer ionic liquids, such as poly(tetrabutylphosphonium3-sulfopropylacrylate) or poly(tributylhexylphosphonium 3-sulfopropylacrylate). Alternatively, solid polymer electrolytes could be used, which include a copolymer of poly(tetrafluoroethylene) with poly(sulphonylfluoride vinyl ether) (commercial example includes Nafion 117 from DuPont), poly (dimethyldiallyammoniuim chloride), plasticized poly (vinylchloride) containing tetrabuylammonium hexafluorophosphate, and poly(ethylene oxide) complex with silver trifluoromethane sulfonate. In some embodiments, the electrolyte 420 contains a reactive chemistry additive and serves as a sensing material (e.g., and neither of the electrodes contains a reactive chemistry additive). In such cases, the presence of the target chemical is detected by measuring a change in a signal (e.g., the capacitance of the circuit) in the sensor 400 due to the change in the electrical properties of the electrolyte. Not to be limited by theory, in some cases, charge arising from electron transfer from a reactive chemistry additive (e.g., a redox mediator material) compound to a target molecule (e.g., the compound of interest (i.e., analyte or target chemical), or products arising from the compound of interest) affects the electrical properties of the electrolyte, thereby affecting the signal in the gas sensor 400. The electrolyte 420 can have as a solvent: water, polar organic solvents, ionic liquids, or polymer electrolytes, for instance. In some embodiments, the electrolyte can be printed from a class of polymer electrolytes or ionic liquids. In some cases, the sensing reactions (i.e., the interaction of the sensing material with the analyte) in any of the gas sensors described herein occur at room temperature and ambient pressure, or at elevated temperatures (e.g., from 30° C. to 80° C.). In some cases, photons (e.g., visible light, or UV light) are introduced to the sensing material of any of the gas sensors described herein to increase the rate of the sensing reactions.

In other embodiments, one or both of the first and second electrodes 410 and 411 serves as a sensing material, and includes a redox mediator, where the redox mediator may be in the form of a polymer or a solution. That is, in some embodiments, at least one of the first electrode, the second electrode, or the electrolyte material contains a redox mediator.

The one or both of the first and second electrodes 410 and 411, or the electrolyte 420 can include a redox mediator, which is a compound that donates or receives a proton or an electron from an electrode and performs reduction or oxidation of a substance in bulk solution away from the electrode by transferring this electron or proton to/away from the substance. FIG. 8 is a table that lists non-limiting examples of possible redox mediators that may be used in the present embodiments. In some embodiments, the redox mediator is an organometallic material, such as a metallocene (e.g., ferrocene). In various embodiments, the redox mediator is a polymer or a solution in which there is non-covalent tethering of the redox mediator to the carbon one or more of the gas sensor components (e.g., the first or second electrodes 410 and 411, and/or the electrolyte 420), covalent tethering, or the redox mediator is untethered to the carbon. Tethering—whether covalent or non-covalent—causes the redox mediator to be immobilized by binding it to a component of the sensor (e.g., the positive electrode). Covalent tethering of the mediator refers to chemically bonding a material that has redox activity to a carbon (e.g., using organic chains comprised of, for instance, combinations of carbon, oxygen, nitrogen, silicon, sulfur, and/or hydrogen).

Figure 9:
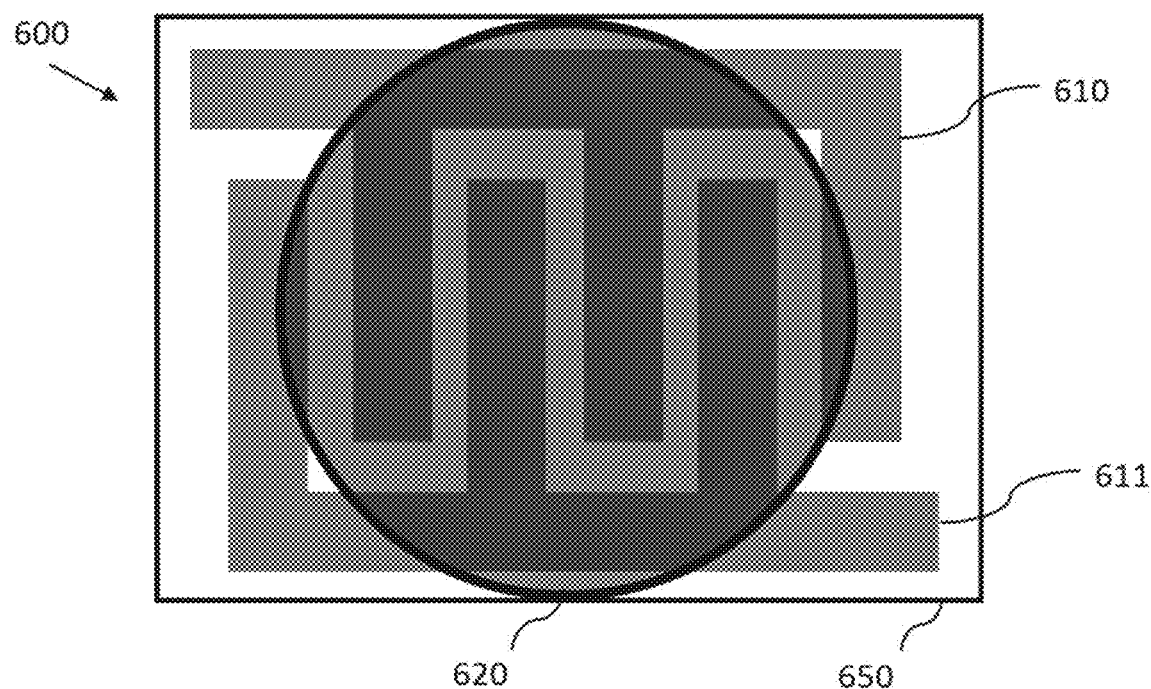
FIG. 9 shows an example of an electrochemical sensor where a first electrode and a second electrode are configured as interdigitated fingers, in accordance with some embodiments.

FIG. 9 shows an example of an electrochemical gas sensor 600 in another embodiment of an electrochemical sensor, where a first electrode 610 and a second electrode 611 are configured as interdigitated fingers to increase the area for electrical interaction between the electrodes, which can be beneficial for example in cases where the electrolyte contains the sensing material (e.g., reactive chemistry additives). Additionally, such an interdigitated electrode geometry can be used to tune the capacitance of the sensor element to allow it to be integrated with other circuit elements more advantageously. In some embodiments, the first and second electrodes 610 and 611 are printed using carbon-based conductive inks (optionally containing one or more redox mediators), as described in relation to the sensor 400 of FIG. 7. An electrolyte 620, which can include a redox mediator (as described in relation to FIGS. 7 and 8), can be printed as a layer over the electrodes 610 and 611. In the illustrated embodiment, the electrolyte 620 is configured as a circular layer (e.g., by applying a droplet of the electrolyte during fabrication of the sensor). However, in other embodiments the electrolyte 620 can be formed (e.g., ink-jet printed or cast) in other geometries, such as a rectangular layer, or other patterned shape to impact the electrical properties of the sensor circuit. Some non-limiting examples of materials for the electrolyte are polymers(e.g., poly (ether urethane) (PEUT), polyepichlorohydrin (PECH), polyisobutylene (PIB), and alkyl cellulose), ceramics, or monomers that solidify into a suitable solid electrolyte. The first electrode 610, second electrode 611, and electrolyte 620 can all be printed on a flexible or rigid substrate 650, where the substrate 650 may be, for example, an $SiO_2$-coated paper or polymeric material.

In some embodiments, the electrodes and electrolytes of the present embodiments contain the particulate carbon described herein, and are tuned to sense the target chemical. In some embodiments, tuning the particulate carbon materials includes functionalizing the particulate carbon to be sensitive to certain materials. For example, the particulate carbon can contain one or more reactive chemistry additives which react with a target chemical to be detected. Some non-limiting examples of target chemicals moieties that can be detected by the sensors of the present disclosure include, but are not limited to, acetone, ammonia, carbon monoxide, ethanol, hydrogen peroxide ($H_2O_2$), nitro ($NO_2$) groups, oxygen, and water (i.e., to detect humidity levels). Characteristic interactions between these chemicals and reactive chemistry additives of one or more of the gas sensor components are used to detect the presence of these chemicals. For example, $NO_2$ groups withdraw electrons, $NH_3$ gas is an electron donor, $CO_2$ gas is an electron donor, acetone is a neutral molecule, $H_2O_2$ is an oxidizer, and ethanol is an electron donor. When a gas species interacts with a reactive chemistry additive in the sensing material, these types of interactions change the electrical properties (e.g., the conductivity, or the complex impedance) of the sensing material, which causes a change in the measured response from the gas sensor indicating the presence of the species.

In an example, a sensing material in a gas sensor contains particulate carbon containing p-type doped graphene semiconductors, which have a response towards $NO_2$, $CO_2$, or $NH_3$ gases. $NO_2$ gas or $NO_2$ containing molecules adsorb/desorb on a graphene surface via three possible adsorption configurations: nitro, nitrite and cycloadditions. During these configurations, there is a charge transfer between $NO_2$ molecules and the p-type graphene molecules. The electron withdrawing effect of $NO_2$ increases the hole-density which leads to a decrease in resistance (or a change in the complex impedance spectrum). $CO_2$ and $NH_3$ are donors, so the resistance of the p-type doped graphene semiconductors increase (or the complex impedance spectrum changes) due to a depletion in hole density.

In another example, a sensing material in a gas sensor contains particulate carbon containing n-type graphene composites, which can be used for acetone sensing. In graphene-zinc-ferrite composites, surface oxygen sp hybrid orbitals interact with acetone to form $CO_2$ and $H_2O$, and release free electrons which decreases the resistance (or change the complex impedance) of the sensing material. In a further example, a graphene composite with iron (II) reacts with $H_2O_2$ to produce $O_2$ and Fe (III). Either $O_2$ can be detected, or UV can be used to check the wavelength of the Fe (III) complex.

In some embodiments, the carbon allotropes within the particulate carbon in the present sensors can be tuned to detect the desired chemical by utilizing a certain microstructure, such as the porosity or curvature (e.g., curved graphene) of the carbon. The carbons can contain sp3, sp2 and/or sp hybrid orbitals, or a combination of these. In other embodiments, tuning can be achieved by adding reactive chemistry additives in the form of functional groups to the carbon, such as oxygen, ketones, or carboxyl. The tuning in the various embodiments may be achieved during initial production of the carbon, and/or by post-processing after the carbon has been made. The post-processing, as described herein, can include steps such as changing the surface area of the carbon material (e.g., by ball milling), changing the conductivity, adding functional groups, or a combination of these.

In an experimental run, a sensor similar to that of FIG. 9 was used to test for the presence of hydrogen peroxide. The interdigitated fingers in this example contained the particulate carbon described herein. The redox mediator solution was 10 μL of 5 mM bis(pentamethylcyclopentadienyl) iron (II), 100 mM tetraethylammonium tetrafluoroborate, and 25 mM KOH in butylmethylimidazolium tetrafluoroborate. The sensor was activated by applying a voltage of 1.0 V in the absence of peroxide and then allowed to equilibrate for 5 minutes to establish a baseline current. The sensor was then put into an atmosphere containing peroxide (single digit parts per million to parts per billion) for 1.0 hr, after which a 1.0 V voltage was applied and the current was measured. The results are shown in Table 1 below.

TABLE 1

Sample experimental results for electrochemical sensor

| | No peroxide | Peroxide vapor present | |
| --- | --- | --- | --- |
| | | Test cycle 1 | Test cycle 2 |
| Current | 2.63 μA | 19.7 μA | 20.5 μA |
| E we | 311 nWh | 1912 nWh | 1973 nWh |

As can be seen from Table 1, the baseline currents increased approximately 650%—from 2.63 μA to 19.7 μA—and remained constant (20.5 μA) for the second hold/test cycle. Thus, the electrochemical sensor demonstrated the ability to detect peroxide with high sensitivity using low amounts of electrical power.

High Frequency Sensors

Some electrochemical sensors utilize direct current (DC) electrical signals to detect changes to a sensing material (e.g., changes in charge carrier concentration causing a change in resistance to indicate chemistry, and/or changes in molecular structure causing a change in capacitance to indicate chemistry). While such DC gas sensors are capable of sensing low levels of chemistry, the detection range without costly equipment (e.g., utilizing high power energy sources) to drive chemical reactions makes widespread adoption impractical for most applications. In the present embodiments, alternating current (AC) signals are used to detect characteristic, reversible impedance responses of a sensing material. In some such gas sensors, a multi-frequency AC signal (e.g., RF current with a range of frequencies) is applied to a sensing material within a sensing circuit and the complex impedance of the circuit is detected. The frequencies of the AC signals used in such "high frequency" gas sensors are typically greater than 1 kHz, or are from 1 kHz to 20 GHz, or are from 100 kHz to 20 GHz.

High frequency gas sensors contain AC circuits with a sensing material incorporated. The geometries and materials in the AC circuits can be tuned to be sensitive to certain frequency ranges, and the complex impedance of the AC circuit changes upon interaction with an analyte that changes the complex impedance of the sensing material. In general, the complex impedance of a material within the AC circuit will affect the signals detected from the circuit and can be tuned to tune the response of the circuit. For example, the sensing material can contain a carbon material, the properties of the carbon material can affect the complex impedance, and therefore the complex impedance of a carbon sensing material and a sensing circuit containing that material can be controlled by specifically tuning the properties of the carbon materials (e.g., the structure of the carbon materials, the types of allotropes present, and the concentration of defects in any ordered carbon allotropes present).

In some embodiments, high frequency gas sensors contain a structured material within the sensing material. The complex impedance of a structured material is a result of the inherent materials properties forming the structure as well as the geometry of the structure, such as the pore size, the pore spacing and the macroscopic shape of the material. In the case of composite structured materials, the distribution of the materials with different properties also affects the complex impedance of the material. For example, electrically conductive materials (e.g., the particulate carbons described herein) can be structured into a mesoporous structure and be decorated with other materials such as dielectrics or permeable materials. In some embodiments, the structure, composition, distribution of materials, and/or the concentration of impurities and/or defects are changed to tune the complex impedance of a structured sensing material within a high frequency gas sensor. Such a structured sensing material is beneficial in high frequency resonant gas sensors because they contain a variety of random paths and path lengths available for conduction at many frequencies, which can provide a sensor with a wide bandwidth of possible frequencies with which to detect a target analyte. In some embodiments, the structured materials (e.g., with the particulate carbon described herein) are frequency selective materials, which are used in high frequency circuits within the present gas sensors.

In some embodiments, dielectric polarization modification impedance spectroscopy is utilized, which is a low-cost method for detecting low concentrations of analytes (e.g., volatile gases or vapors) in a gas sensor. In some embodiments, an impedance spectroscopy measurement can be used to detect the modulation of properties of a sensing material containing reactive chemistry additives (e.g., a structured sensing material containing particulate carbon and a redox mediator in the presence or absence of an analyte). For example, selective frequency interrogations of S21 (i.e., the transmission of a high frequency signal through an AC circuit or system) and S11 (i.e., the reflectance of a high frequency signal from an AC circuit or system) can be used to detect a change in the complex impedance of the sensing material and/or circuit (or system) as a whole. The operation of the gas sensor relies on a change in the measured S21 or S11 value upon exposure to an analyte.

The combination of such high frequency gas sensors (e.g., utilizing impedance spectroscopy) and the unique properties of the particulate carbon described herein (e.g., structure, surface area, and conductivity) enables gas sensors that are able to generate the same results as the more costly counterparts (e.g., detecting an analyte with concentrations in the parts per million (ppm) or parts per billion (ppb) ranges) at a greatly reduced price, and an improved ease of adoption and portability. The low power requirement of the present embodiments allows for the system to be powered by battery systems and in some cases using energy harvester systems. Additionally, the imaginary part of the complex impedance of the sensing materials described herein have spectral signatures (e.g., peaks in the spectra) that can discriminate one molecular arrangement from others, enabling the detection of several molecules with one sensor.

Figure 10:
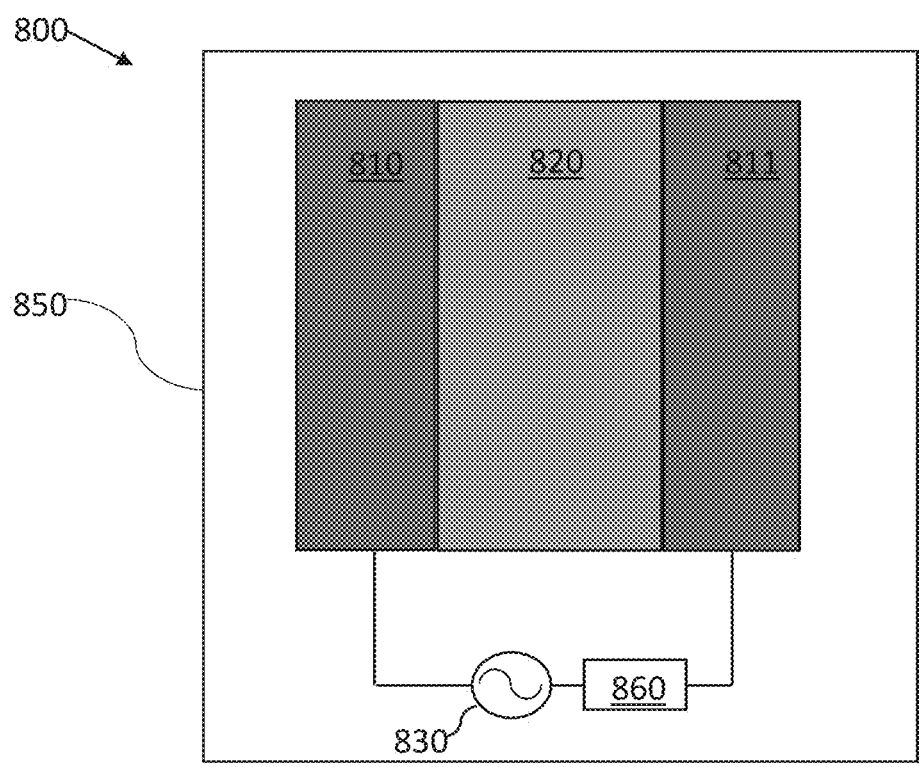
FIG. 10 shows an example of a chemical sensor in which high frequency spectroscopy is used as the detection method, in accordance with some embodiments.

FIG. 10 shows an example embodiment of a chemical sensor 800 in which high frequency (e.g., impedance) spectroscopy is used as the detection method. Sensor 800 includes a first electrode 810, a second electrode 811, and a dielectric 820 sandwiched between the electrodes 810 and 811, all of which are arranged on substrate 850. In some embodiments, the electrodes 810 and 811 and/or the dielectric 820 are printed from inks on the substrate 850. Substrate 850 may be rigid or flexible, for example, a label. In some cases, a device may be formed on both sides of a substrate. In some embodiments, the electrodes 810 and 811 contain the particulate carbon described herein), silver particles, metal particles, conductive oxide particles (e.g., indium tin oxide and/or fluorine-doped tin oxide particles), or other conductive particulate materials (including any aspect ratio particulates, such as those shaped as spheroids, rods, and wires). In other embodiments, one or both of the electrodes 810 and 811 contain a carbon allotrope such as, but not limited to, graphene, graphene oxide, carbon nano-onions, and/or carbon nano-tubes. In some embodiments, one electrode includes a metal while the other electrode does not. One or both electrodes 810 and 811 and/or dielectric 820 can include a reactive chemistry additive (e.g., a redox mediator), as described in reference to the electrochemical sensors above, which is tuned to one or more target analyte (e.g., volatile gas or vapor) species.

In operation, an AC source 830 applies AC signals having a range of frequencies (e.g., greater than 1 kHz, or from 10 kHz to 20 GHz, or from 10 kHz to 1 GHz, or from 500 kHz to 20 GHz, or from 500 MHz to 20 GHz) to the sensor 800, and a detection circuit 860 detects a change in impedance at specified frequencies when the target substance interacts with (e.g., is absorbed into, or adsorbed onto) the sensing material. In some embodiments, the sensor 800 uses an impedance spectroscopy technique, in which specific target analyte chemicals interact with the sensing material (e.g., containing the particulate carbon described herein) causing a change in the complex impedance of the sensing material. The change in the complex impedance can then be measured by the circuitry 860, and the measured change used for detecting the target substance. In some embodiments, the sensing material contains tailored carbon and a reactive chemistry additive with electrons that interact with the target compound and change the resonance frequency.

High Frequency Resonant Sensors

One type of a high frequency gas sensor is a resonant gas sensor. In some embodiments, a resonant gas sensor contains one or more sensing materials, and changes to the resistivity and permittivity of the sensing materials result in changes to the resonant behavior of the sensor. In some embodiments, such a resonant gas sensor can be printed and utilize small electronics (e.g., a small IC chip), such that it can be miniaturized and produced at low cost. Such low cost miniature resonant gas sensors have a myriad of applications including product labels on food packaging, shipping labels on packages, and portable hazardous/toxic gas sensors. In some embodiments, low cost resonant gas sensors are enabled by the particulate carbon materials described herein, which improve the resonant gas sensor sensitivity allowing for low power signals to produce adequate responses. For example, the high the surface area and mesoporous structure of the particulate carbon allows more analyte vapors to enter into the structure and increases the changes in the sensing material resistivity and permittivity for a given analyte concentration. In some embodiments, the sensing materials or materials making up the other elements (e.g., with the particulate carbon described herein) contain frequency selective materials, which are used to tune the resonant frequencies of the resonant circuits within the present gas sensors.

In some embodiments, the resonant gas sensors contain pickup electrodes to provide AC signal power input to the sensing materials and detect an output from the sensing materials. The geometries of the constituent elements can be tuned in order to produce a resonant structure with certain frequency response in the sensor. In addition, the materials properties (e.g., resistivity and/or complex permittivity) of the sensing material can also be tuned to form a resonator structure or composite with a certain spectral frequency response. Tuning the materials properties and resonant structure geometries can be advantageous to enhance the performance of the gas sensor to be more sensitive in certain frequency ranges.

In some embodiments, a resonant gas sensor system includes a microprocessor, which provides a signal to a transducer (i.e., an antenna) that drives a sensing material in the resonant gas sensor over a specific frequency range. The microprocessor can also detect the response (e.g., the complex impedance spectrum of the sensor). In different cases, the response can be a reflected AC signal (i.e., S11) or a transmitted AC signal (i.e., S21). The sensing material can be integrated into the transducer or be a separate element. Different resonant gas sensor architectures are described below. In some cases, the response is compared to a database (i.e., a library) of resonance spectra for a variety of molecular chemistries related to certain molecules of interest (e.g., those in explosives, or rotting foods). In some embodiments, the functionality of the detector and transducer are integrated into a single, monolithic, patterned film structure, optionally integrated with other electronics such as an integrated microprocessor and/or communication chip (e.g., to communicate a detection event to another device). The microprocessor (and other optional integrated electronics) can be powered using an integrated battery or using energy harvesting structures (e.g., using an antenna that absorbs RF energy or a photocell that absorbs light, coupled to an integrated capacitor to store the harvested energy). In some cases, such an integrated sensor can contain a resonant structure with engineered properties (e.g., conductivity, and geometry) to minimize the antenna absorption loss at high frequency.

In some embodiments, a resonant gas sensor contains a set of electrically conductive elements that form a resonant structure. The resonant structure itself exhibits resonance or resonant behavior, that is, it naturally oscillates at some frequencies, called its resonant frequencies, with greater amplitude than at others. These resonant structures within the sensors are used to select specific frequencies from a signal (e.g., the signal provided by the microprocessor in the resonant gas sensor systems described herein). For example, a resonant gas sensor can contain two conductive electrodes surrounding and/or electrically coupled to a dielectric or an electrically conductive gas sensing material, all of which form a single resonant structure (along with other components of the system, in some cases). In another example, a transducer (i.e., an antenna) can be excited with a signal, and the sensing material can be arranged adjacent to the transducer such that the complex impedance of the sensing material impacts a detected response. In some cases, the electrode(s) and/or the gas sensing material can contain the particulate carbon described herein. In some cases, the electrode(s) and/or the gas sensing material can be printed and/or be deposited from a liquid, gas or ink dispersion.

In some cases, the resonant structures described above can be incorporated into the resonant gas sensor circuit to form an LC tank circuit. For example, a coiled antenna can be used as an inductive element, and a sensing material between two electrodes can be used as a capacitive element, and the inductive and capacitive elements can be connected in parallel or in series to form a tank circuit in a resonant gas sensor. In some embodiments, a single transducer structure (e.g., a coiled antenna) can contain (or be formed from) the sensing material, and also provide the inductive and capacitive elements of the tank circuit. Such multi-functional transducers can be driven by a microprocessor, and upon interaction with an analyte the transducer material properties change, which change the characteristic response of the gas sensor circuit, which in turn can be measured by detection circuitry to detect the presence of an analyte. In other cases, the transducer does not contain sensing materials, and the sensing materials change the properties of one or more elements within the tank circuit (e.g., the capacitance of a capacitive element), which change the characteristic response of the circuit, which in turn can be measured by detection circuitry to detect the presence of an analyte.

When a gas sensitive material interacts with an analyte, the complex electrical materials properties of the permittivity $\varepsilon=\varepsilon'-j\varepsilon''$ (where j is the imaginary unit) and permeability $\mu=\mu'-j\mu''$ change. In a resonant gas sensor, the varying material properties can lead to a change in the wave propagation of a signal (e.g., a multi-frequency signal provided by a microprocessor) through a resonant structure (e.g., an LC tank circuit, an antenna, or a microstrip line). In addition to the materials properties, the wave propagation of a signal in a resonant gas sensor also depends on the geometry of the structures formed by the elements of the sensor. In some cases, the resonant structures in the resonant gas sensor contain one or more waveguides, and the wave propagation of a signal also depends on the design of the waveguide(s). Generally, electromagnetic waves are guided to a desired transmission mode by restricting their expansion in one or two dimensions. One transmission structure for waves with a transversal electromagnetic mode (TEM) is the planar microstrip line, consisting of a strip conductor and a ground plane either separated by a dielectric substrate or separated by a dielectric material on a single side of a substrate. The two-dimensional structure of microstrips make them well suited for miniaturization and integration with other components and, because of the planar structure, they can be fabricated conventionally by thick or thin film technology. In some cases, the circuit elements (e.g., resonant structures) are formed (e.g., by printing) on one side of a substrate to create a resonator (e.g., a microstrip line with co-planar electrodes separated by a dielectric gap), while in other embodiments, the elements are formed (e.g., by printing) on both sides of a substrate to create a resonator (e.g., a patch antenna separated from a ground plane electrode by a dielectric substrate containing a sensing material). The substrate can be many different materials including rigid or flexible materials, those with suitable dielectric properties, a polymer sheet, or paper. In some cases, a base layer can be pre-deposited on the substrate to act as an anchoring layer to absorb part of the deposited (e.g., printed) material and or to create a barrier to prevent absorption of the deposited material into the substrate (e.g., paper).

Figure 11A:
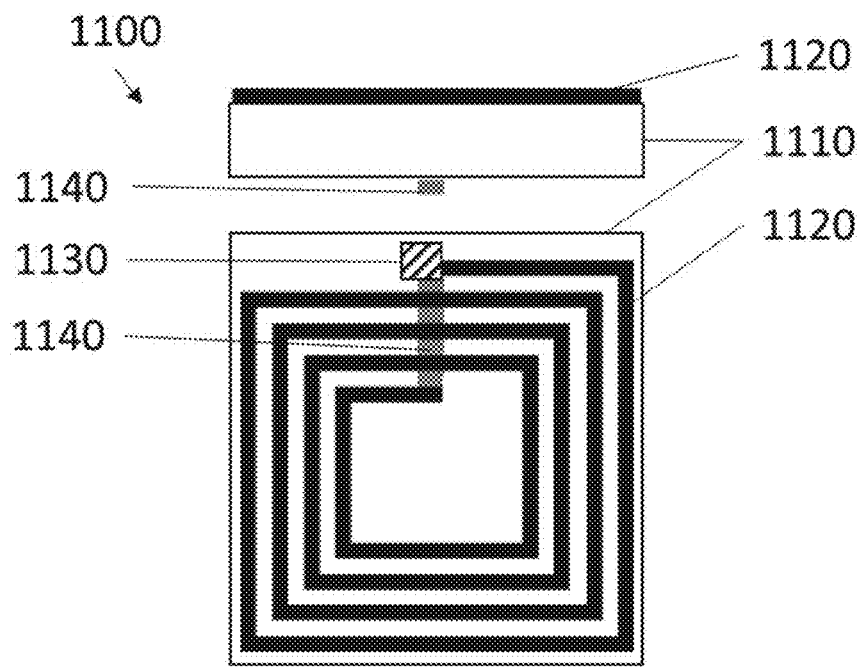
FIG. 11A shows a non-limiting example of a resonant gas sensor in side view and plan view, in accordance with some embodiments.

FIG. 11A shows a non-limiting example of a resonant gas sensor 1100 in side view and plan view, including a substrate 1110, a transducer 1120, a microprocessor 1130, and a ground electrode 1140, in accordance with some embodiments. A first terminal of the microprocessor 1130 is electrically coupled to a first terminal of the transducer 1120, and the ground electrode 1140 completes the circuit from a second terminal of the transducer to a second terminal of the microprocessor 1130. In this example, the ground electrode is connected to the second terminal of the transducer 1120 and to the second terminal of the microprocessor 1130 through vias in the substrate (not shown). The transducer 1120 in this example is a spiral with successive loops with different dimensions. The microprocessor 1130 provides AC signals at different frequencies to the first terminal of the transducer 1120, and measures the response (either reflected from the transducer 1120 or transmitted through the transducer 1120, in different embodiments). In this example, the transducer 1120 contains a sensing material (e.g., a redox mediator), which is sensitive to an analyte, such that when the resonant gas sensor 1100 is exposed to the analyte, the complex impedance of the transducer 1120 changes, and the response detected at the microprocessor 1130 changes indicating the detection of the analyte. In other words, the complex permittivity and/or permeability of the sensing material changes upon exposure to an analyte, which changes the resonant frequency of the sensor circuit indicating the detection of the analyte.

Figure 11B:
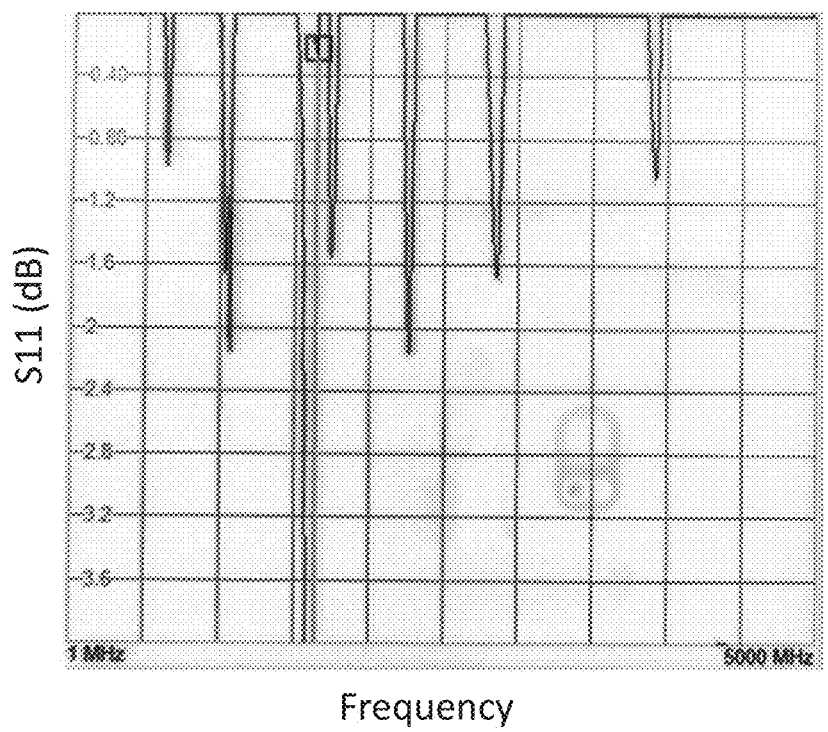
FIG. 11B shows an example of a response from a resonant gas sensor in the presence of an analyte of interest, in accordance with some embodiments.

FIG. 11B shows an example of a response from a resonant gas sensor (e.g., 1100 in FIG. 11A) in the presence of an analyte of interest. The x-axis in the plot in FIG. 11B is frequency (from 1 MHz to 5000 MHz), and the y-axis is the reflected signal from the transducer (e.g., element 1120 in FIG. 11A) (i.e., S11, which is the signal reflected back from the first terminal of the transducer) in dB. The troughs in the plot in FIG. 11B indicate the resonant frequencies of the circuit, where the AC signals are not reflected (e.g., dissipated) in the resonant circuit. These troughs can change depending on the type and concentration of an analyte present, and in some cases can be compared to a library to determine the identity of a detected analyte species. Since the location of the troughs depends on the resonant frequencies of the entire gas sensor circuit, in some embodiments, a library of analyte species and concentrations is created for a specific resonant gas sensor design and materials set.

Figure 11C:
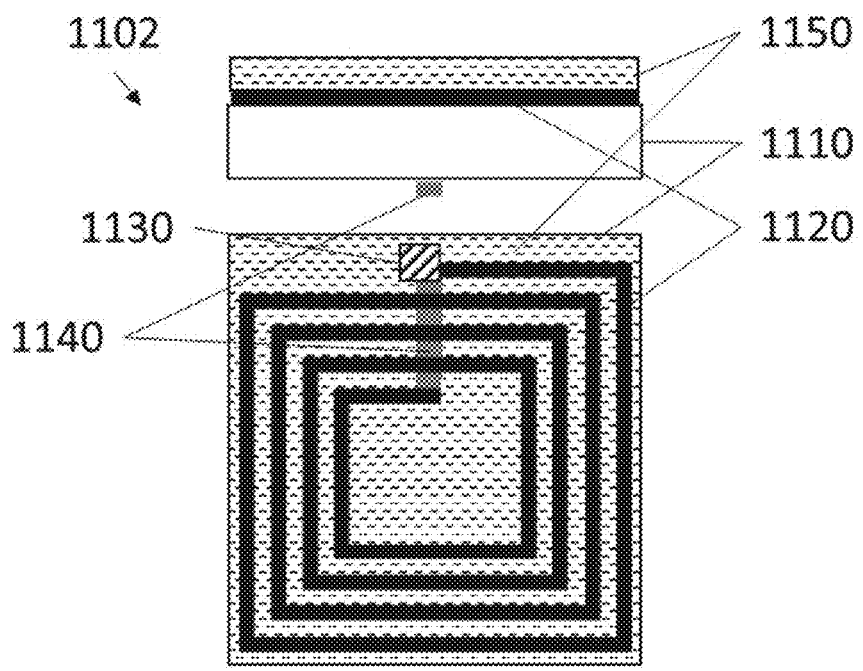
FIGS. 11C and 11D show non-limiting examples of resonant gas sensors in side view and plan view, in accordance with some embodiments.

FIG. 11C shows a non-limiting example of a resonant gas sensor 1102 in side view and plan view, including a substrate 1110, a transducer 1120, a microprocessor 1130, a ground electrode 1140, and a sensing material 1150, in accordance with some embodiments. The resonant gas sensor 1102 is similar to the resonant gas sensor 1100, and further includes a separate sensing material 1150 disposed above and in between successive loops of the spiral transducer 1120. In this example, the sensing material is sensitive to an analyte, such that when the resonant gas sensor 1102 is exposed to the analyte, the frequency response of the resonant circuit formed by the transducer 1120 and sensing material 1150 changes, and the response detected at the microprocessor 1130 changes indicating the detection of the analyte. The change in frequency response in this example can be caused by a change in the inductance of the transducer 1120 and/or a change in the capacitance between successive loops of the transducer 1120, which change the resonant frequencies of a tank circuit formed by the transducer 1120 and sensing material 1150. In other words, the complex permittivity and/or permeability of the sensing material changes upon exposure to an analyte, which changes the resonant frequency of the sensor tank circuit indicating the detection of the analyte.

Figure 11D:
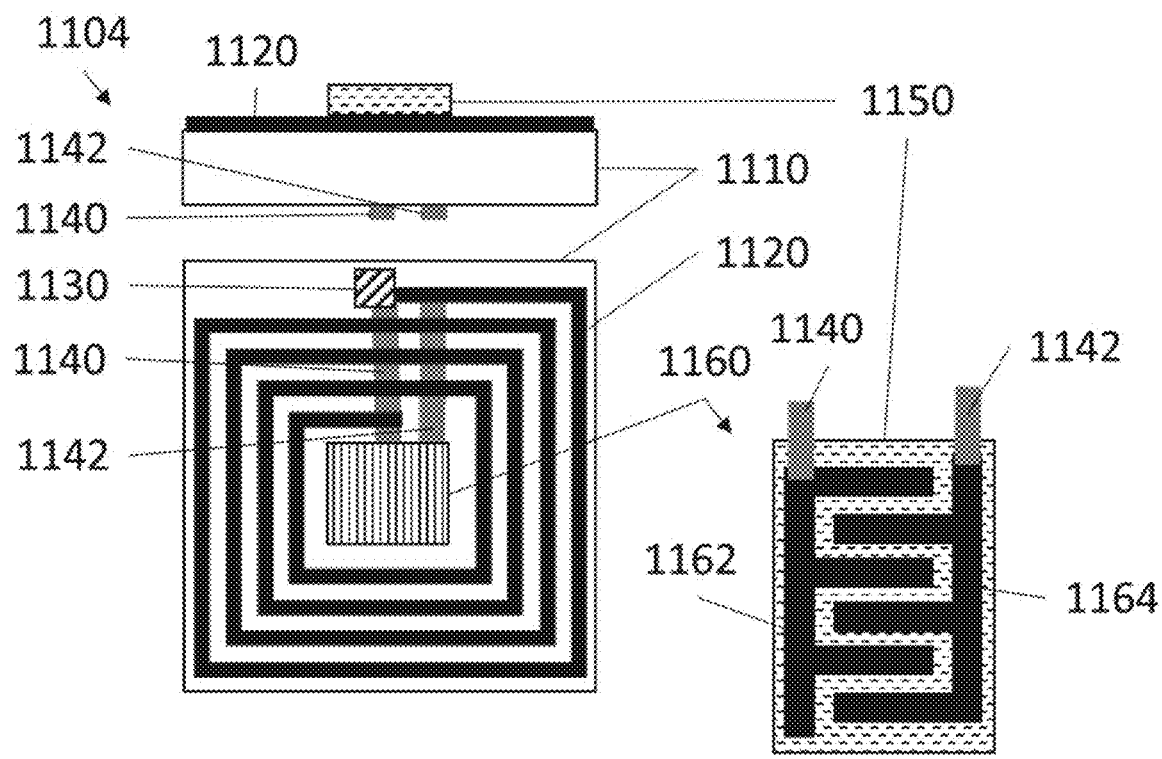

FIG. 11D shows a non-limiting example of a resonant gas sensor 1104 in side view and plan view, including a substrate 1110, a transducer 1120, a microprocessor 1130, a ground electrode 1140, a second electrical connection 1142, a sensing material 1150, and a capacitive element 1160, in accordance with some embodiments. The resonant gas sensor 1104 is similar to the resonant gas sensor 1100, and further includes a capacitive element 1160. The capacitive element 1160 in this example is formed from interdigitated electrodes 1162 and 1164. In this example, the capacitive element 1160 has the sensing material 1150 disposed on and between the interdigitated fingers 1162 and 1164. In this example, the capacitive element 1160 is wired in parallel with the transducer 1120; the ground electrical connection 1140 is electrically coupled to electrode 1162 of the capacitive element 1160, and the second electrical connection 1142 couples the electrode 1164 of the capacitive element 1160 to the first terminal of the transducer 1120 (as described in resonant gas sensor 1100 in FIG. 11A). Therefore, an LC tank circuit (with the inductive element and capacitive element in parallel) is formed from the transducer 1120 and the capacitive element 1160 in this example. In this example, the sensing material 1150 (e.g., a redox mediator) is sensitive to an analyte, such that when the resonant gas sensor 1104 is exposed to the analyte, the capacitance of the capacitive element 1160 changes, and the response detected at the microprocessor 1130 changes indicating the detection of the analyte. In other words, the complex permittivity and/or permeability of the sensing material changes upon exposure to an analyte, which changes capacitance of the capacitive element 1160 and the resonant frequency of the sensor tank circuit indicating the detection of the analyte. One advantage of separate inductive and capacitive elements (e.g., as shown in resonant gas sensor 1104) is that the resonant frequency of the tank circuit can be tuned. One example of this is lowering the resonant frequency to a lower frequency range (e.g., from about 20 GHz to about 1 GHz) to reduce the cost of the electronics required to drive the sensor circuit.

Figure 11E:
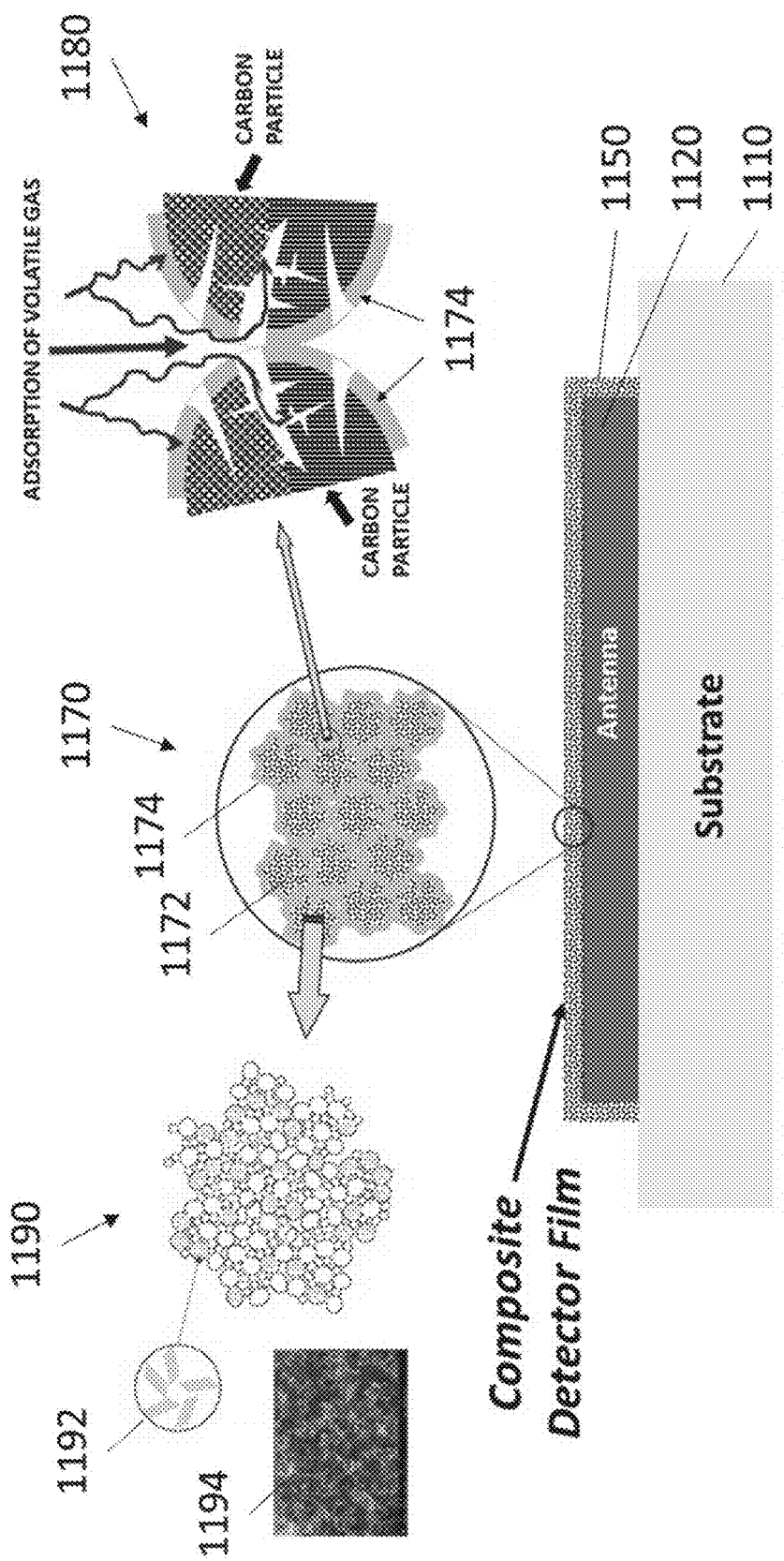
FIG. 11E shows a non-limiting example of a resonant gas sensor with a sensing material containing particulate carbon, in accordance with some embodiments.

FIG. 11E shows a non-limiting example of a resonant gas sensor containing a substrate 1110, a transducer antenna 1120, and a composite detecting film 1150 for sorption of an analyte (e.g., volatile organic solvent vapors), in accordance with some embodiments. The composite detecting film 1150 contains a structured particulate conducting phase encapsulated with a polymeric binder. Insets 1170 and 1180 show schematics of the particulate conducting phase 1172 encapsulated by the polymer binder 1174. Inset 1180 shows a volatile gas (or more generally, an analyte) adsorbed by the polymer binder and/or the interior surfaces of the particulate carbon. In some embodiments, the polymer binder contains one or more reactive chemistry additives, which interact with an analyte and cause the electrical properties of the sensing material 1150 to change. In other embodiments, a reactive chemistry additive (e.g., a dissolved salt) can be deposited on and within the pores of the particulate carbon. In some cases, the reactive chemistry additives can be incorporated into the particulate carbon and the polymer binder to further improve the sensitivity of the sensing material. In some cases, the reactive chemistry additive can be added to the particulate carbon and the sensing material can contain the particulate carbon and no polymer binder. Inset 1190 shows schematics of graphene sheets 1192 and the porous 3-dimensional structure 1194 of the particulate carbon in the composite detecting film 1150. Some non-limiting examples of the structured particulate conducting phase can contain 3-dimensionally structured microporous or mesoporous graphene-containing particles, or the particulate carbon described herein. Some non-limiting examples of polymeric binder include PEUT, PECH, PIB, and alkyl cellulose. Such structures are beneficial to detect analyte species and concentration in resonant gas sensors because they produce characteristic, reversible impedance responses that can be measured (or transduced) with a high frequency (resonant) antenna element.

Figure 11F:
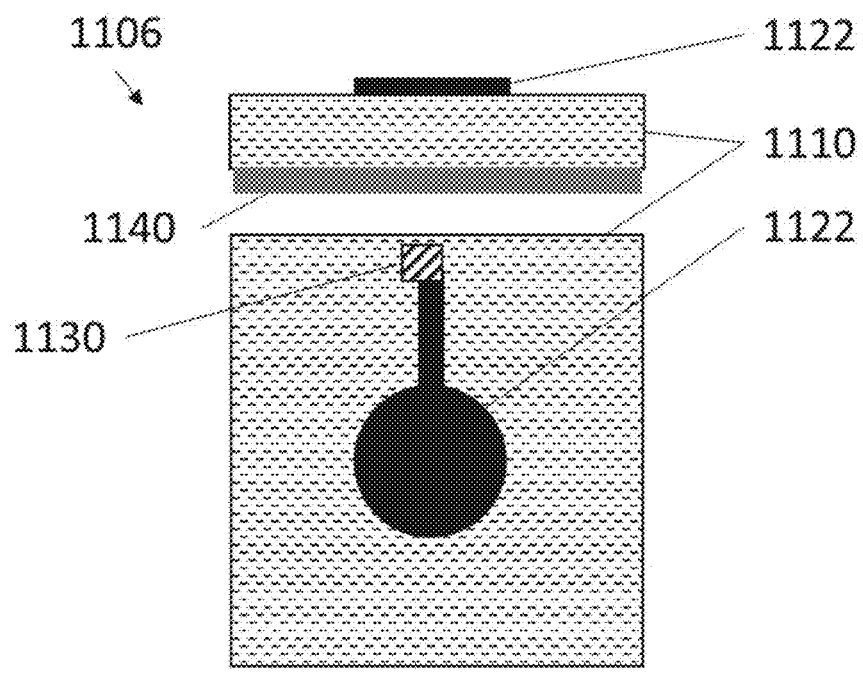
FIG. 11F shows a non-limiting example of a resonant gas sensor in side view and plan view, in accordance with some embodiments.

FIG. 11F shows a non-limiting example of a resonant gas sensor 1106 in side view and plan view, including a substrate 1110, a transducer 1122, a microprocessor 1130, a ground electrode 1140, and a sensing material 1150, in accordance with some embodiments. The resonant gas sensor 1106 contains similar elements to those in resonant gas sensor 1100, however, the transducer 1122 in this example is a patch antenna in the shape of a circle, which is electrically coupled to a first terminal of the microprocessor, rather than a spiral antenna. The ground plane is formed from ground electrode 1140 on the opposite side of substrate 1110, and is coupled to a second terminal of the microprocessor through a via in the substrate (not shown in the figure). The substrate 1110 in this example contains the sensing material. In this example, the sensing material 1150 (e.g., a redox mediator) is sensitive to an analyte, such that when the resonant gas sensor 1106 is exposed to the analyte, the frequency response of the resonant circuit formed form the transducer 1122 and the sensing material 1150 changes, and the response detected at the microprocessor 1130 changes indicating the detection of the analyte. Similar to the examples shown in FIGS. 11A, 11C and 11D, the response can either be reflected from the patch antenna transducer 1122 back to the first terminal of the microprocessor, or be transmitted through the patch antenna transducer 1122 and be detected at the second terminal of the microprocessor (connected to the ground electrode 1140), in different embodiments.

The resonant gas sensors described in FIGS. 11A, 11C, 11D and 11F are non-limiting examples only, and many other variations exist. For example, the electrodes, transducers, capacitive elements and/or substrates can contain sensing material in any of the above examples. In such examples, the sensing material itself can be patterned to affect the resonant frequencies of the gas sensor circuit. Additional elements can also be added, for instance, to provide additional sensing materials that can affect the response from the circuits in the above examples. The electrodes, transducers, capacitive elements and/or substrates in any of the above examples can contain the particulate carbon described herein. The electrodes, transducers, capacitive elements and/or substrates can be formed in many different shapes as well. For example, the transducers can be rectangular spiral antennas (e.g., as shown in FIGS. 11A, 11C and 11D), square spiral antennas, ovular spiral antennas, or other types of spiral antennas. The patch antenna transducers can be circular (e.g., as shown in FIG. 11F), rectangular, square, ovular, or other patch-like shapes. Other transducer shapes are also possible, such as patterns that are resonant at particular frequency ranges. In some cases, more than one transducer can be driven by a single microprocessor, and multiple signals from the circuits containing the multiple transducers can also be detected by a single microprocessor. The circuits can also contain waveguides (e.g., microstrip lines) instead of simple electrical connections (e.g., as shown in FIGS. 11A, 11C, 11D and 11F) to conduct the AC signals between elements in the gas sensor circuits. The geometry of the waveguides can be designed such that there is low loss of the AC signals between elements in the circuits. The capacitive elements can also be different types than that shown in FIG. 11D. For example, a 3-dimensional capacitor can be formed with structured electrodes surrounding a sensing material, to further increase the surface area of the capacitor and further improve the capacitance change upon exposure to an analyte. The circuits also can be electrically coupled by direct connections (e.g., as shown in FIGS. 11A, 11C, 11D and 11F), or can be coupled through a dielectric material (since the AC fields can extend outside of a waveguide or other resonant structure.

In some embodiments, the transducers used in the gas sensors described herein are one or more of the antennas or transducers described in U.S. application Ser. No. 15/944,482, entitled "Microwave Chemical Processing," which is assigned to the same assignee as the present application, and is incorporated herein by reference as if fully set forth herein for all purposes.

Figure 12A:
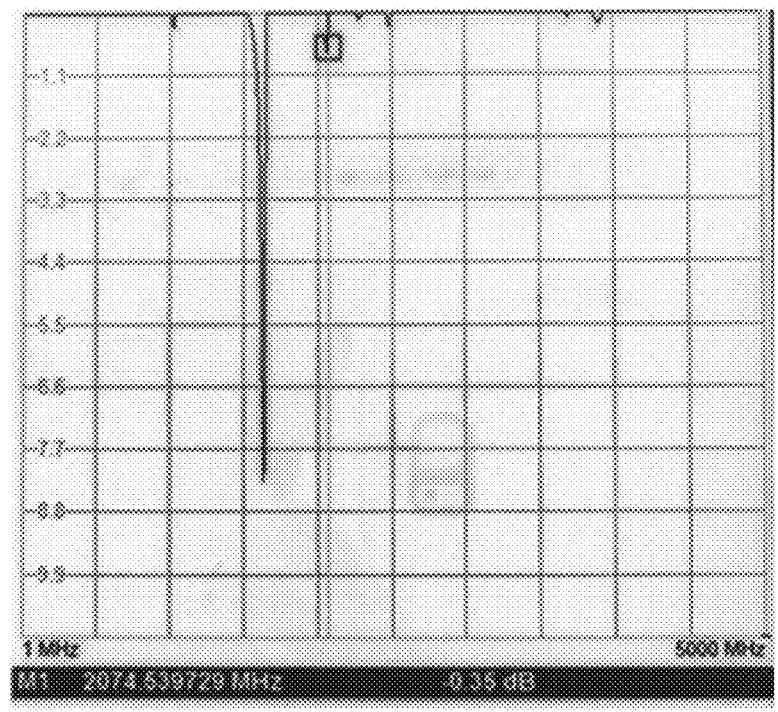
FIGS. 12A-12C show a time evolution of example spectra produced when an analyte is detected by a resonant gas sensor, in accordance with some embodiments.
Figure 12B:
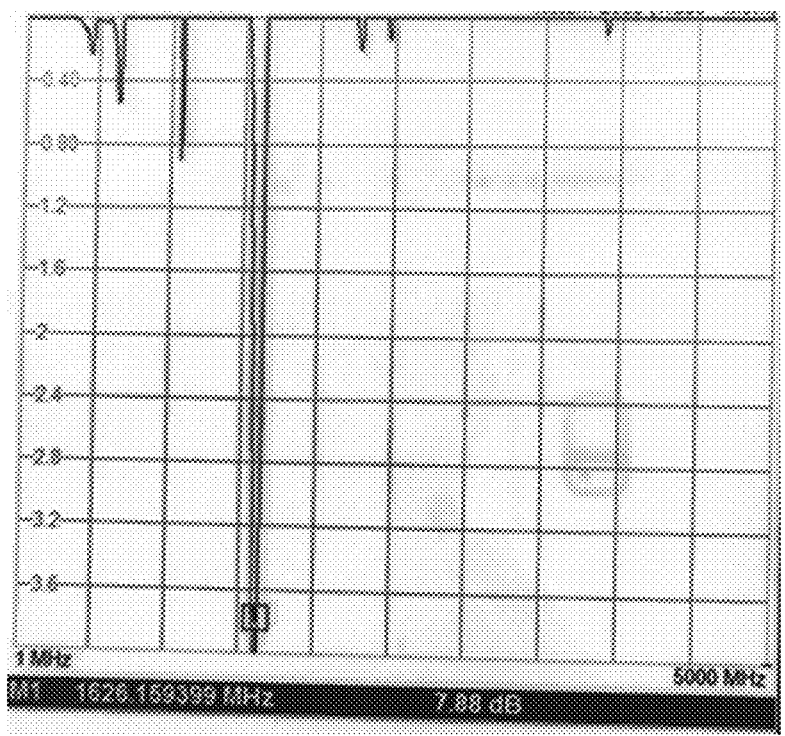
Figure 12C:
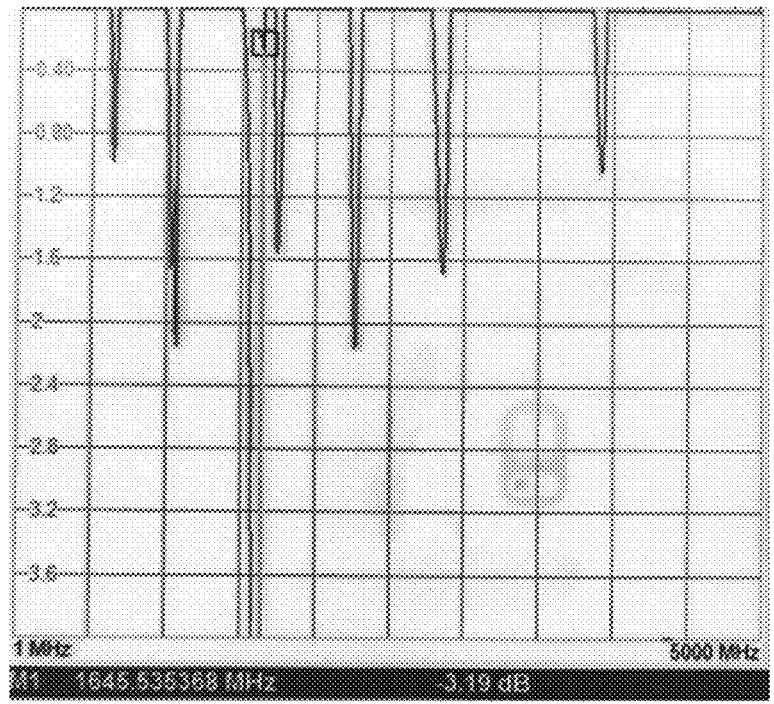

FIGS. 12A-12C show a time evolution of example spectra produced when an analyte was detected by a resonant gas sensor similar to that shown in FIG. 11D, but the system in this example used a separate virtual network analyzer rather than an integrated microprocessor. The resonant gas sensor in this example contained a substrate that was paper with a silica layer deposited on the surface, and a printed spiral transducer and capacitive element connected in parallel. The capacitive element contained a sensing material with the particulate carbon described herein and a reactive chemistry additive containing PEUT. The analyte in this example is isopropyl alcohol mixed with acetone and water. FIGS. 12A, 12B and 12C show the reflected signal (i.e. S11) from the circuit after about 1-2 seconds, about 15 seconds and about 30 seconds, respectively. In the absence of any analyte the signal is a flat line with no features at 0 dB. FIG. 12A shows some evidence that an analyte is present after only about 1-2 seconds. Therefore, the design and materials of the resonant gas sensor in this example enable a fast detection of an analyte. FIG. 12C shows multiple peaks representative of the analyte detected, and illustrates the capability of this type of resonant gas sensor to identify a species of analyte (e.g., by comparing a detected spectrum with those in a stored library).

The AC signals used by the resonant gas sensors described above contain a set of frequencies (e.g., in a range from 1 MHz to 20 GHz), and the method by which the signal is applied can vary. For example, a single frequency sweep can be performed continuously, or periodically at various intervals (e.g., once every 1 second, 10 seconds, 1 minute, 10 minutes, or once an hour). In some cases, different sweeps with different resolutions (i.e., frequency spacing between the different frequencies within a range) can be performed at different intervals.

In one non-limiting example, a first coarse sweep is performed followed by targeted sweeps. Other similar methods for supplying different frequencies to a resonant gas sensor are also possible in different embodiments. In this example, a first fast/coarse sweep of the frequency range is performed by the microprocessor, and a peak is detected. After the first coarse sweep, the microprocessor can drive the resonant sensor to the peak and dither around it to more accurately ascertain the peak frequency and relative intensity values. Ascertained peak values can be compared to a library of possible analytes, and in some cases, if the library indicates a possible match, the microprocessor can be used to sweep to a second peak in the spectrum of a possible analyte to obtain a second indicator as a check to reduce the number of false positives. The peak values (and/or other features of measured spectra) are compared to a library of possible analytes using an integrated microprocessor (e.g., as shown in FIGS. 11A, 11C, 11D or 11F), or communicating with a remote processor and/or database. Such a method containing a first coarse scan followed by targeted subsequent dither scans can be beneficial to provide high detection accuracy with lower power requirements than performing a fine scan over a large set of potential analyte resonant frequencies. To further save power, such a method can be performed periodically (e.g., once every 1 second, 10 seconds, 1 minute, 10 minutes, or once an hour). In some embodiments, the system requirements can be relaxed to further save cost and power by targeting a +/−20% accuracy level for the concentration of a measured analyte. Although such a system may not provide highly accurate concentrations, it can have low power requirements (e.g., less than 1 nW, or less than 1 pW) and have a low production cost (e.g., less than 1 US dollar per unit, or less than 5 US dollars per unit, depending on the complexity of the system and the number of analytes capable of being detected), and therefore still be useful in many applications where indication and detection of an analyte are needed and an accurate concentration measurement is not required (e.g., to detect the presence of an explosive inside of a mailed package, or detecting the occurrence of food spoilage in a packaged food product).

Chemiluminescence Sensors

Figure 13:
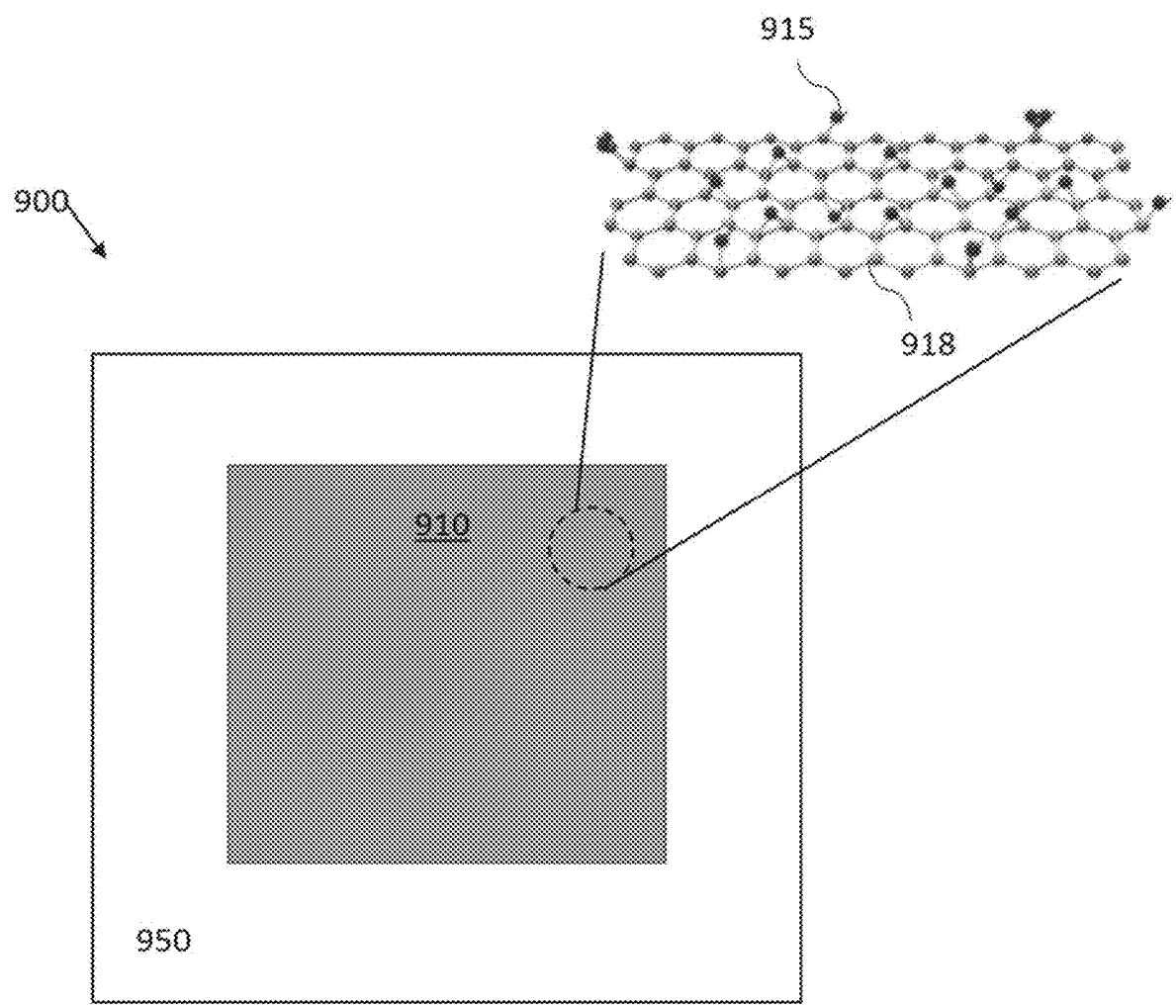
FIG. 13 shows a non-limiting example of a chemiluminescent gas sensor, in accordance with some embodiments.

Other embodiments include chemiluminescent sensors as shown in FIG. 13. The sensor 900 includes a chemiluminescent composite material 910 printed on a substrate 950. The material 910 includes a luminescent dye material 915 tethered to a graphene-based material 918, where the dye material is chosen based on being a receptor for a certain target chemical molecule. In some embodiments, the graphene-based material 918 is contained within the particulate carbon described herein. Detection of various functional groups of a target chemical is indicated by a wavelength shift in the absorption spectra of the dye. Due to electron transfer, there is a change in the structure and excitation energy of the dye. In other words, due to the presence of electron donating and withdrawing groups, the electronic state of the dye is changed, causing the change in color and wavelength. Some non-limiting example compounds for luminescent dyes include, for example, Ru(Bpy)3, or analogues of it; or Au, Cu or Ag pyrazolytes. For example, peroxidase or chemical vapors in contact with metalloorganic luminescent material can coordinate, resulting in a wavelength shift which can be visually observed. In some cases, the dye-sensitized graphene sheets, such as graphene oxide, are carboxyl-group functionalized. Due to the high surface area and beneficial structure of the particulate carbon described herein, the composite material provides a structure that results in higher sensitivity than conventional chemiluminescent sensors.

Sensor Systems

Figure 14:
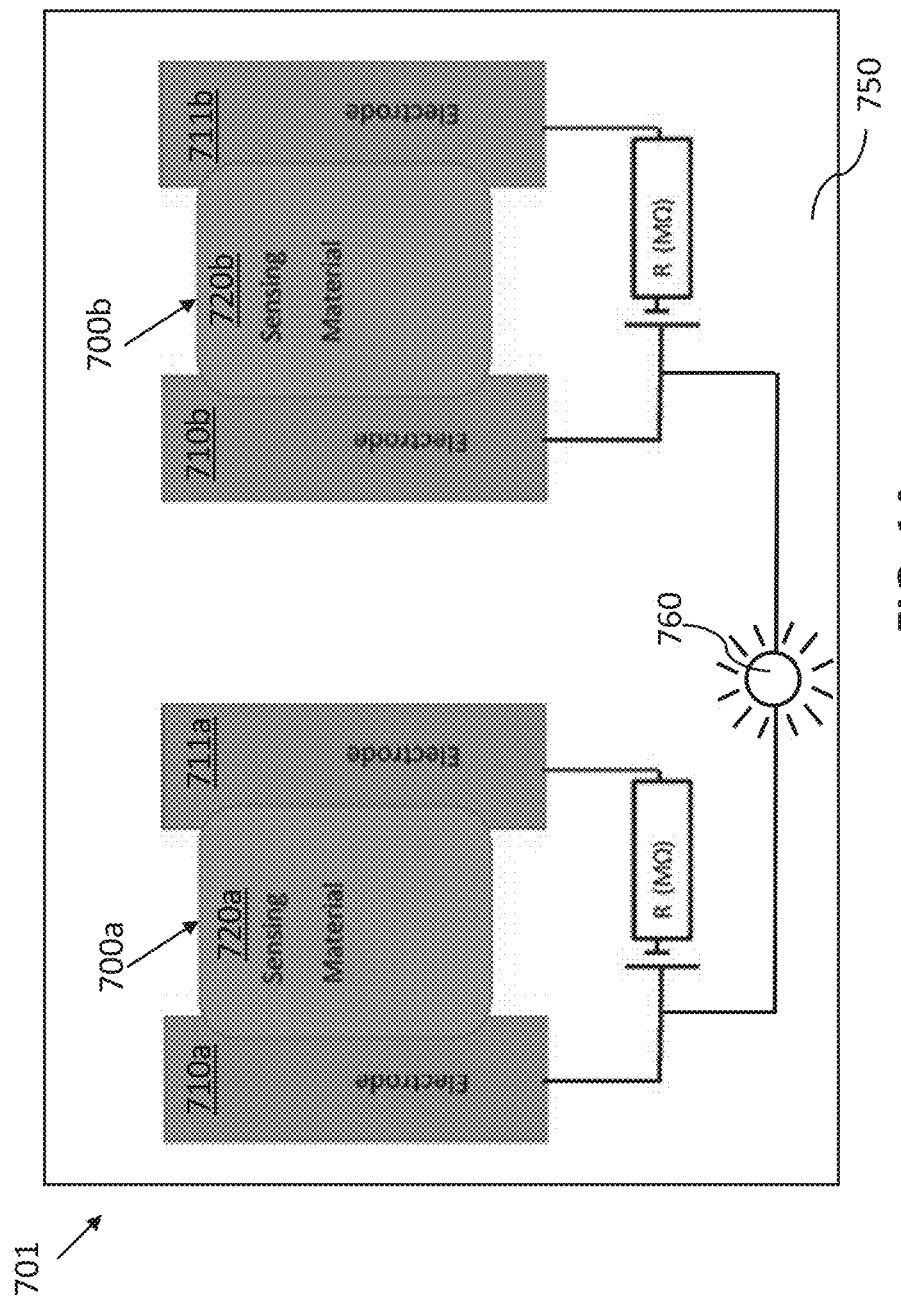
FIG. 14 shows a non-limiting example of a sensor system in which multiple individual chemical sensors are used for detecting an analyte, in accordance with some embodiments.

FIG. 14 shows a non-limiting example embodiment of a sensor system 701 in which multiple individual gas sensors are used for detecting one or more chemical compounds (i.e., various analytes). Sensor system 701 includes a first sensor 700a for detecting a first target chemical, and a second sensor 700b for detecting a second target chemical. In this embodiment, both first sensor 700a and second sensor 700b are electrochemical sensors, but other types of sensors, described herein, can also be used. For example, the gas sensors of the sensor system may be electrochemical, high frequency, resonant, chemiluminescent, or a combination of these. In some cases, first sensor 700a and second sensor 700b are printed on the same substrate 750, such as a label. Each sensor 700a/b can include a first electrode 710a/b, a second electrode 711a/b, and an electrolyte 720a/b, where the components include particulate carbon and redox mediators as described in relation to FIG. 7. Although two sensors 700a and 700b are shown in this example, more than two sensors can also be included. In some embodiments, an array of sensors can be used to add functionality, such as the ability to detect multiple gases, subtract a background level of moisture and/or improve the sensitivity to an analyte. Furthermore, other non-printed sensors, such as IR sensors, can be included. As one example, an IR sensor can be included to detect $NO_2$ groups.

An indicator 760 is coupled to sensors 700a and 700b through electrical circuitry (not shown), where both sensors 700a and 700b must positively sense detection of their target chemical in order for the indicator 760 to be activated. The combination of all the individual target substances being present indicates that a certain compound is present. Types of indicators 760 that may be used include an optical indicator (e.g., a light emitting diode), an acoustic output, or a visual display such as a text or graphic read-out. In other embodiments, the indicator 760 may be part of the sensor devices, such as if the individual sensors themselves can provide a positive indication of detection through a color change of the sensing material, or other indicator mechanism. The sensor system 701 represents embodiments in which the presence of multiple sensors in one device are utilized to detect a combination of chemicals, in order to characterize an overall compound. The presence of multiple sensors can also help rule out false positives.

In the sensor systems for detecting a chemical compound in some embodiments, the sensor systems include a first sensor configured to detect a first target chemical, a second sensor configured to detect a second target chemical that is different from the first target chemical, and a substrate on which the first sensor and the second sensor are printed. An indicator indicates when both the first sensor positively detects the first target chemical and the second sensor positively detects the second target chemical.

Additionally, other components can be integrated with the gas sensors to add functionality to a gas sensors system. Some non-limiting examples of electro-active labels containing the present gas sensors, that also contain a display-based human/machine interface are devices that can display telemetry, Q-codes or bar codes, and/or icons. Example scenarios include telemetry, where information can be updated, and/or have an image such as a gage; a Q-code (QR code) or bar code, using digital data or number/text formats; and icons for packages where a color or image change is displayed. In these various scenarios, a change in the display, such as in the symbol or color, or a back-and-forth change, can be used to indicate the condition of the product. These display telemetry devices are a new approach to providing information about the contents of a package status, using a microprocessor-based machine and user detection of the conditions within a package. The present devices can also optionally include low power communications components (e.g., to communicate directly with other electronic devices).

In a non-limiting example, a cardboard shipping box was equipped with an electrochemical sensor similar to that shown in FIG. 9, a resonant sensor similar to that shown in FIG. 11D, integrated microprocessors to drive the sensors and detect signals from the sensors, a display to communicate visual information (e.g., a species of analyte detected) and a wireless communication chip (i.e., a Wi-Fi chip) to communicate information to other devices. The electronics were powered by an integrated battery. The sensing material in the electrochemical sensor and the resonant sensor in this example were both printed and both contained the particulate carbon described herein. The beneficial properties of the particulate carbon coupled with the sensor designs enabled them to utilize low power (e.g., with currents from 0.1 microamps to 5 microamps) to detect analyte species. This example illustrates that gas sensors utilizing the particulate carbon described herein can be produced using low cost low power driver/detection electronics that can be integrated into a small package. Furthermore, this example showed that such low cost printed gas sensors can also be integrated with other system components such as displays and communication chips.

Printing of Chemical Sensors

In some embodiments, gas sensor components (e.g., electrodes and sensing materials) are printed from carbon-based inks (e.g., containing the particulate carbons describe herein). The electrical components of the present gas sensors can be printed on backing materials such as labels, and integrated with other hardware components on a substrate. More than one sensor can be printed on the same substrate, such as multiple sensors of the same type, or different types of sensors (e.g., electrochemical, high frequency, chemiluminescent). Types of substrates—which also may be referred to as backing materials—include rigid or flexible substrates, card stock, labels, or other types of materials used for printing.

In some embodiments, printed gas sensor components containing the particulate carbon described herein are further processed after printing to increase the conductivity of the printed components. For example, particulate carbon containing electrodes, transducers, and/or capacitive elements of the resonant gas sensors described herein can be further processed after initial printing to increase the conductivity of these printed components. In some embodiments, the transducers described herein require high conductivities (e.g., greater than 3500 S/m, or greater than 5000 S/m, or greater than 10000 S/m, in different embodiments) in order to perform as effective transducers, and in some cases these conductivities cannot be reached using printed particulate carbon without further processing. Some non-limiting examples of processes to improve the conductivity of printed particulate carbon materials are sintering and/or calendaring. For example, sintering can be performed using a plasma, laser or microwave energy. In some cases, the sintering process can locally heat the printed material and not substantially affect the substrate and/or other underlying materials. In other embodiments, calendaring is performed to increase the conductivity of the printed carbon materials. For example, calendaring using a heated roller, or a roller equipped with an energy source (e.g., microwave energy) to sinter and calendar simultaneously can increase the conductivity of the printed particulate carbon.

In other embodiments, high conductivity printed gas sensor components can be formed by printing a mixture of the present particulate carbon with other conductive particles added to increase the conductivity of the printed components. For example, the electrodes, transducers, and/or capacitive elements of the resonant gas sensors described herein can be formed using such mixtures. Some non-limiting examples of conductive particles that can be mixed with the particulate carbon described herein are Ag, Sn and/or Sb particles. Printed components for gas sensors containing the particulate carbon and additional conductive particles can be advantageous in some embodiments because the particulate carbon provides beneficial structure to the printed components (e.g., high surface areas), and the conductive particles improve the conductivity of the printed components.

The devices can be designed to operate in low power ranges, such as 0 to 1 volts, or less than 100 μW, or less than 1 μW. In some cases, the low power consumption is made possible by the high conductivity, the high surface area and mesoporous structure of the carbon-based materials used in printing the components, the small size of the devices, the choice of detection methodologies, and optionally the choice of display technologies. The overall device architecture may also use low power technology for the various system components (e.g., gas sensor and indicator).

In some embodiments, the printed components are made from carbon-based inks and can be electrically coupled to each other and/or to one or more additional hardware components, which can be mounted on the substrate. The hardware components can be, for example, one or more of an output display, microcontroller units (MCU), switches, and capacitors, among others. The hardware components use information stored in, generated by, and/or communicated from the printed components, such as by processing or displaying data from the printed components. The present devices can also optionally include low power printed communications components.

In addition to the particulate carbon described herein, types of carbon materials for the various embodiments of printed components can include, but are not limited to, graphene, graphenes (graphene-based materials), graphene oxide, reduced graphene oxide, graphite oxide, graphite intercalation compounds, graphite, graphane, carbon nano-onions, diamond, p-type diamond, n-type diamond, glassy carbon, amorphous carbon, activated carbon, carbon black and/or carbon nano-tubes, sulfur-based carbons (e.g., sulfur melt diffused carbon), and carbons with metal (e.g., nickel-infused carbon, carbon with silver nanoparticles, graphene with metal). The printed components can be printed by, for example, screen printing or ink-jet printing.

Reference has been made to embodiments of the disclosed invention. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A sensor for detecting an analyte, comprising:
  a flexible substrate; and
  a resonant gas sensor, comprising:
    a transducer arranged on the flexible substrate, the transducer including a first terminal configured to receive a plurality of alternating current (AC) signals from an external AC source;
    a sensing material electrically coupled to the transducer, the sensing material including a first particulate carbon and a reactive chemistry additive; and
    a ground electrode electrically coupled to a second terminal of the transducer.

2. The sensor of claim 1, wherein the first particulate carbon includes one or more carbon aggregates, each carbon aggregate comprising a plurality of carbon nanoparticles.

3. The sensor of claim 1, wherein the reactive chemistry additive comprises a redox mediator.

4. The sensor of claim 1, wherein the flexible substrate comprises paper or a flexible polymer.

5. The sensor of claim 1, wherein the sensing material is contained within a polymer binder.

6. The sensor of claim 1, wherein the reactive chemistry additive is tuned to one or more analytes.

7. The sensor of claim 1, wherein the sensor comprises a printed shipping label or a printed food-packaging label.

8. The sensor of claim 1, wherein the transducer comprises a spiral antenna.

9. The sensor of claim 8, wherein at least a portion of the sensing material is disposed between successive loops of the spiral antenna.

10. The sensor of claim 1, further comprising a capacitive element coupled to the transducer.

11. The sensor of claim 10, wherein the capacitive element and the transducer comprise a tank circuit.

12. The sensor of claim 11, wherein the tank circuit is configured to indicate exposure of the sensor to the analyte based at least in part on changes in a resonant frequency of the tank circuit.

13. The sensor of claim 10, wherein the capacitive element includes a pair of interdigitated electrodes.

14. The sensor of claim 13, wherein at least a portion of the sensing material is disposed between one or more fingers of the interdigitated electrodes.

15. The sensor of claim 1, wherein the resonant gas sensor further comprises a detection component configured to receive one or more AC signals reflected or transmitted from the transducer.

16. The sensor of claim 15, wherein the detection component is configured to indicate the exposure of the sensor to the analyte based at least in part on a complex impedance of the sensing material.

17. The sensor of claim 15, wherein the detection component is configured to indicate exposure of the sensor to the analyte based at least in part on the one or more AC signals reflected or transmitted from the transducer.

18. The sensor of claim 17, wherein the detection component is configured to indicate the exposure of the sensor to the analyte based at least in part on a resonant frequency of the one or more AC signals reflected or transmitted from the transducer.

19. The sensor of claim 18, wherein the resonant frequency is indicative of a type of the analyte exposed to the sensor.

20. The sensor of claim 18, wherein the resonant frequency is indicative of a concentration of the analyte exposed to the sensor.

* * * * *